United States Patent
Baril et al.

(10) Patent No.: US 9,784,654 B2
(45) Date of Patent: Oct. 10, 2017

(54) METHOD FOR TREATING AT LEAST ONE BIOLOGICAL SAMPLE CONTAINING A TARGET MICROORGANISM

(71) Applicant: BioMérieux, Marcy l'Etoile (FR)

(72) Inventors: Florent Baril, Saint Jean de Niost (FR); Bruno Colin, Marcy l'Etoile (FR); Jean-Pierre Flandrois, Lyons (FR); Thomas Junillon, Lyons (FR); Benoît Mallen, Tassin la Demi Lune (FR); Edgard Minassian, Lentilly (FR); David Mosticone, Saint Consorce (FR); Antoine Vimont, Saint Malo (FR)

(73) Assignee: Biomerieux, Marcy-l'Etoile (FR)

( * ) Notice: Subject to any disclaimer, the term of this patent is extended or adjusted under 35 U.S.C. 154(b) by 0 days.

(21) Appl. No.: 14/441,492

(22) PCT Filed: Nov. 7, 2013

(86) PCT No.: PCT/EP2013/073316
§ 371 (c)(1),
(2) Date: May 7, 2015

(87) PCT Pub. No.: WO2014/072438
PCT Pub. Date: May 15, 2014

(65) Prior Publication Data
US 2015/0292994 A1    Oct. 15, 2015

(30) Foreign Application Priority Data

Nov. 7, 2012  (FR) ..................... 12 60566

(51) Int. Cl.
*B01F 11/00*    (2006.01)
*G01N 1/40*     (2006.01)
(Continued)

(52) U.S. Cl.
CPC .......... *G01N 1/405* (2013.01); *B01F 11/0065* (2013.01); *C12M 23/14* (2013.01);
(Continued)

(58) Field of Classification Search
CPC .... B01F 11/0065; C12M 23/14; C12M 27/02; C12M 41/44; C12M 27/00
See application file for complete search history.

(56) References Cited

U.S. PATENT DOCUMENTS 3,518,393 A * 6/1970 Barclay ................. A61M 5/445
                                                     219/772
3,819,158 A * 6/1974 Sharpe ................. B01F 11/0065
                                                     206/221
(Continued)

FOREIGN PATENT DOCUMENTS

EP    1693072 A1    8/2006
FR    2781695 A1    2/2000
(Continued)

OTHER PUBLICATIONS

International Search Report mailed Jan. 28, 2014 for International Patent Application No. PCT/EP2013/073316.

*Primary Examiner* — Charles Cooley
(74) *Attorney, Agent, or Firm* — Pepper Hamilton LLP

(57) ABSTRACT

One embodiment provides a device for processing at least one biological sample capable of containing at least one target microorganism within at least one container. The device having at least one displacement device for generating the displacement of the contents of the at least one container and at least one site for receiving the at least one container. Additionally, the at least one container can receive the at least one biological sample within the at least one container, the container being delimited by a wall fixed on a base. Further, the at least one displacement device may be movable with respect to the base, and the at least one (Continued)

container may include a flexible material which allows the at least one container to be compressed against said wall.

4 Claims, 8 Drawing Sheets

(51) Int. Cl.
    *C12M 1/00*     (2006.01)
    *C12M 1/06*     (2006.01)
    *C12M 1/34*     (2006.01)
    *G01N 33/569*     (2006.01)

(52) U.S. Cl.
    CPC ............ *C12M 27/02* (2013.01); *C12M 41/12* (2013.01); *C12M 41/36* (2013.01); *C12M 41/44* (2013.01); *G01N 33/56911* (2013.01); *G01N 33/56916* (2013.01)

(56) References Cited

U.S. PATENT DOCUMENTS

| | | | | |
|---|---|---|---|---|
| 3,830,475 A * | 8/1974 | Inoue | ...................... | A61C 5/066 206/219 |
| 3,946,780 A * | 3/1976 | Sellers | ............... | B65D 51/1616 383/102 |
| 5,057,429 A * | 10/1991 | Watanabe | ............. | B01F 9/0001 206/213.1 |
| 5,523,228 A * | 6/1996 | Ingram | .................. | C12M 23/14 435/297.1 |
| 5,533,804 A * | 7/1996 | Larsson | ............... | A61M 1/1656 366/274 |
| 5,547,108 A * | 8/1996 | Gsell | ..................... | A61M 1/029 222/105 |
| 6,142,661 A * | 11/2000 | Lafond | ............... | B01F 11/0065 366/197 |
| 6,190,913 B1 * | 2/2001 | Singh | .................. | B01F 11/0017 435/383 |
| 6,267,498 B1 * | 7/2001 | Lafond | ............... | B01F 11/0065 366/197 |
| 6,273,600 B1 * | 8/2001 | Sharpe | ................ | B01F 11/0065 366/117 |
| 6,345,734 B2 * | 2/2002 | Schalow | ....................... | 222/103 |
| 6,416,212 B1 * | 7/2002 | Rogers | ............... | B01F 11/0065 366/117 |
| 6,439,759 B1 * | 8/2002 | Ray | ..................... | B01F 11/0065 366/197 |
| 6,634,783 B2 * | 10/2003 | Baron | ................ | B01F 11/0045 222/105 |
| 7,195,394 B2 * | 3/2007 | Singh | .................. | B01F 11/0017 366/211 |
| 7,377,686 B2 * | 5/2008 | Hubbard | ............... | A61M 1/025 366/208 |
| 7,799,521 B2 * | 9/2010 | Chen | ....................... | B01L 3/502 435/286.5 |
| 9,073,023 B2 * | 7/2015 | Bernard | ................ | B01F 3/1207 |
| 9,175,253 B2 * | 11/2015 | Hata | ....................... | B01L 9/523 |
| 9,228,166 B2 * | 1/2016 | Barrett | .................... | C12M 23/14 |
| 9,238,789 B2 * | 1/2016 | Niazi | ..................... | C12M 27/20 |
| 9,550,969 B2 * | 1/2017 | Chotteau | ................ | C12M 23/14 |
| 9,587,283 B2 * | 3/2017 | Niazi | ....................... | C12Q 3/00 |
| 2003/0036192 A1 * | 2/2003 | Singh | .................. | B01F 11/0017 435/297.2 |
| 2003/0214874 A1 * | 11/2003 | Hlavinka | .............. | A61L 2/0011 366/197 |
| 2007/0128718 A1 * | 6/2007 | Courtois | ................ | C12M 23/14 435/325 |
| 2007/0140047 A1 * | 6/2007 | Ray | ..................... | B01F 11/0065 366/197 |
| 2008/0160597 A1 * | 7/2008 | van der Heiden | .. | B01F 11/0025 435/252.8 |
| 2008/0186802 A1 * | 8/2008 | Bungay | ............... | B01F 11/0065 366/142 |
| 2011/0080800 A1 * | 4/2011 | White | ................. | B01F 11/0065 366/207 |
| 2013/0244322 A1 * | 9/2013 | Henon | ................... | C12M 23/14 435/325 |
| 2013/0316446 A1 * | 11/2013 | Andersson | ............. | C12M 23/14 435/305.1 |
| 2014/0349280 A1 * | 11/2014 | Raymond | ................ | C12Q 1/00 435/5 |
| 2015/0292994 A1 * | 10/2015 | Baril | .................... | B01F 11/0065 435/6.12 |
| 2015/0329893 A1 * | 11/2015 | Colin | ...................... | B01L 3/502 435/31 |
| 2016/0106624 A1 * | 4/2016 | Camisani | ............. | A61M 1/025 435/325 |
| 2016/0152935 A1 * | 6/2016 | Roosloot | ............... | C12M 23/14 435/297.1 |

FOREIGN PATENT DOCUMENTS

| | | | |
|---|---|---|---|
| SU | 1681937 A1 * | 10/1991 | .......... B01F 11/0065 |
| WO | WO 00/15328 A1 | 3/2000 | |
| WO | WO 2005/056748 A1 | 6/2005 | |
| WO | WO 2008/003696 A1 | 1/2008 | |
| WO | WO 2012/027847 A1 | 3/2012 | |
| WO | WO 2015133116 A1 * | 9/2015 | ............ C12M 23/14 |
| WO | WO 2016062833 A1 * | 4/2016 | ............ C12M 23/14 |

* cited by examiner

METHOD FOR TREATING AT LEAST ONE BIOLOGICAL SAMPLE CONTAINING A TARGET MICROORGANISM

CLAIM OF PRIORITY

The present application is a National Stage filing under 35 U.S.C. §371 of International Patent Application No. PCT/EP2013/073316, filed on Nov. 7, 2013 and entitled "METHOD FOR TREATING AT LEAST ONE BIOLOGICAL SAMPLE," which claims the benefit of and priority to French Patent Application No. 1260566, filed on Nov. 7, 2012 and entitled "METHOD FOR TREATING AT LEAST ONE BIOLOGICAL SAMPLE," both of which are incorporated by reference herein in their entireties.

TECHNICAL FIELD

The present invention concerns, generally, the processing of biological samples (for the purposes of enrichment and/or analysis), as well as the analysis of these biological samples, for example in the field of microbiology and more particularly that of industrial microbiology.

PRIOR ART

The raw products used and the processed products marketed by the agri-food industry (meat products, dairy products, seafood products, plant products, etc.), as well as the pharmaceutical and cosmetic products and water intended for drinking, are subjected to numerous microbiological tests in order to be certain of their harmlessness (absence of pathogenic bacteria, or of degradation, absence of bacteria which are markers of contamination endangering health, absence of toxins).

The microbiological analysis of these products requires precise techniques, of which the time to obtain the result must be as short as possible.

In the medical field, it is necessary to anticipate and diagnose the risk of infection: the faster and more precise the diagnosis, the more effective the care of the patient and the more the risk of transmission is minimised. The approach is similar for animal health in the veterinary field.

In the food field, the issue is identical. However, it differentiates between:
- pathogenic microorganisms (such as *Salmonella* or the *E. coli* O157:H7 strain) and their toxins, the search for which applies to the raw materials, intermediate products, marketed finished products,
- non-pathogenic microorganisms, which are used as quality indicators of the production process, from the raw materials to the finished products, all along the chain,
- bacteria of technological interest as enzymes,
- microorganisms which are contamination markers.

The fast and precise detection of suspected contaminations (within food batches) makes it possible to inspect them and thus to take corrective action at short notice.

Technically, microbiological analysis generally implements one or more phases of pre-enrichment and/or enrichment, one or more detection phases, and one or more microorganism enumeration phases. For particular applications, such as agri-food microbiological inspection, a confirmation phase may also be required in order to meet the standards in force in this field.

The detection phase is based historically on the growth (culture) of microorganisms on essentially agar media, and by revealing the metabolic characters of the microorganisms sought. Specific enzymatic substrates are conventionally used. These substrates may be compounds used in the bacterial metabolism and leading to a modification of the medium detected by indicators (variation of pH, reduction, precipitation, etc.). In other cases, these enzyme substrates are made up of two parts, a first part which is specific to the enzyme activity to be revealed, also called the target part, and a second part which acts as a marker, called the marker part, generally constituted by a chromophore or a fluorophore. By choosing these substrates on the basis of whether or not a reaction takes place, it is possible to characterise the nature of a microorganism or to distinguish between different groups of microorganisms. Thus the appearance or disappearance of coloration or of fluorescence shall indicate a genus or a type of microorganisms. In this respect, the use of chromogenic media makes it possible to simultaneously detect and identify the germs sought. It simplifies the process and substantially reduces the time to obtain the result. By way of concrete example, the applicant's ChromID® media will be cited. These chromogenic media are based on the detection of metabolic characters specific to the germs sought, such as for example beta-glucuronidase enzyme activity for *Escherichia coli*.

Immunoassays constitute another of the technologies used for the detection test. They make use of the immunogenic characteristics of the microorganisms sought. Non-exhaustively, competition or sandwich-type ELISA ("Enzyme Linked Immuno Sorbent Assay") techniques may be cited.

Finally, the molecular biology techniques, based on the genomic characters of the microorganisms sought, are also implemented to detect and identify the target microorganisms. These molecular biology techniques offer extremely interesting prospects. By way of example, it is possible to cite conventional amplification techniques such as PCR ("Polymerase Chain Reaction" in English) and NASBA ("Nucleic Acid Sequence Based Amplification" in English), which may be coupled with real-time detection techniques known to the person skilled in the art.

The confirmation phase, for its part, is more particularly attached to microbiological analysis in the agri-food field. In fact, when the result of the methods developed above is positive, it is necessary to confirm the presence of the pathogen sought. This imposes a complementary test and the use of a detection principle different from that used during the first analysis. The techniques described above are used at will for the confirmation.

The full and precise identification of a microorganism in a sample therefore requires a sequence of several steps: enrichment, detection and, where applicable, confirmation. The standardisation of the tests routinely used has enabled automation of the detection methods which, however, remain long to implement. One disadvantage of the conventional analysis methods used in the prior art resides in the fact that the enrichment, detection and, where applicable, confirmation steps are carried out sequentially and require a large number of time-consuming handling operations, thus affecting the time necessary to produce results.

As indicated above, the detection phase is generally preceded by at least one pre-enrichment and/or enrichment phase (more generally called enrichment phase or step for the purposes of the present application). The latter is crucial insofar as, at the present time, there is no method for detecting a target microorganism in a biological sample, present in a minimal quantity, for example in the order of several cells, without resorting to a prior enrichment step. This enrichment phase requires the use of culture media, which are selective or non-selective (depending on the aim sought), which aim to promote the growth of the target microorganisms in the biological or environmental samples, while limiting the growth of non-target flora. The culture media are frequently used in sterile plastic bag-type containers, in which they are placed in contact with the food or environmental samples, with the aim of suspending and enriching the microorganisms sought. As mentioned above, this enrichment phase is necessary in particular in order to reveal the presence of at least one target microorganism in a highly variable and potentially very large quantity of sample, for example from 25 grams (g) to 375 g diluted in a culture medium volume of between 225 and 3375 milliliters (mL). At the end of this enrichment step, an aliquot (generally of a volume of between 5 microliters (μL) and 5 mL) is conventionally sampled in order to implement the target microorganism detection step. In this aliquot, it is necessary to have a sufficient quantity of target microorganisms in order to ensure their systematic detection.

This enrichment step requires not only an ad hoc culture medium but also an incubation of the assembly formed at least by the biological sample and the culture medium at an optimal temperature to allow the growth of the target microorganism(s). The incubation generally takes place at a temperature ranging from 25 to 45° C. for a predetermined period of time (for example from 6 h to 48 h). During this incubation period, no supplementary action is performed on the sample. This period of time is therefore not harnessed, it is in a manner of speaking "wasted". This goes against the problem presented above, which aims to develop a precise and fast analysis technique. Indeed, during this enrichment step, the sample is immobilised in an oven without a means of intervention because this step generally takes place overnight.

Further, in particular when it is desired to analyse a biological sample, the molecules of which exhibit a high intercohesion, for example a solid or semi-solid sample, it is necessary to provide, before the enrichment step, a so-called "kneading" step (high-strength homogenisation), during which the structure of the biological sample is partially or totally altered. This step of kneading the sample is aimed at homogenising the sample to be analysed in a diluent (the culture medium) and releasing the bacteria into the liquid. This step guarantees the accessibility of the nutrients of the culture medium to the germs present in the sample, and in particular to the target microorganisms (e.g. *Salmonella* spp, *Listeria* spp, etc.). This step is ensured by the use of kneading devices (also called kneaders), the three main types of which are the following:

Stomacher®,
mixer and
Pulsifier®.

However, the use of such kneaders presents certain disadvantages, including:

necessity to "knead" one sample at a time,
presence of several devices to reduce the total analysis time (problem of cluttering the laboratory space),
the kneading time is short (from 30 seconds to 1 minute) but extremely violent, whereby this violence of the kneading risks bringing about a deterioration of the sample matrix, which can cause interference on the detection means, depending on the detection method used (for example PCR inhibitors in molecular biology). Moreover, the violence of conventional "kneading" generates a lot of noise in the laboratory, which disrupts the work of laboratory personnel, in the presence of certain samples (seeds, pastes), the violence of the kneading sometimes causes perforation of the plastic pouch.

Further, the conventional methods of microbiological analysis frequently require the use of selective media intended to target the microorganism(s) of interest. Generally, the selective agents are provided from the start of enrichment and at low concentration, so at a concentration which is not well suited to allow both inhibition of additional flora and optimal growth of the microorganisms to be detected. As is known to the person skilled in the art, microorganisms—including the target microorganisms—are referred to as "stressed" when they are present in the sample to be analysed. This is particularly the case after the aforementioned kneading step. In this state of stress, the target bacteria are particularly fragile and sensitive, notably to the presence of selective agents. It is therefore tricky—or even inappropriate—to place a biological sample to be analysed in direct contact with a selective medium. Further, the stressed microorganisms directly in contact with the selective agents exhibit a latency phase before more substantial growth, which is detrimental to their growth and thus possibly to their detection. In order to make sure of the presence or absence of the target microorganisms, it is therefore necessary to increase the enrichment/incubation time, which correspondingly delays the detection and/or identification of the microorganisms of interest.

Consequently, to obtain the level of selectivity sought, a method comprising at least two steps has been developed in the prior art. This comprises:

a primary enrichment phase, during which the biological sample is introduced into a primary enrichment medium lacking selective agent (for example peptone water),
a secondary enrichment phase consisting of subculturing an aliquot of the primary enrichment medium in a second enrichment medium (secondary enrichment medium) containing selective agents.

Generally, when it is necessary to perform a secondary enrichment, the latter is performed only the day after (d+1), when the technician returns to his workstation. This method considerably increases the incubation time and consequently delays the detection time and, where applicable, identification time of the target microorganism(s). Further, the step of subculturing the primary enrichment medium in a secondary enrichment medium can lead to handling errors, and also represents a source of error for the sample traceability.

To decrease the total incubation time and reduce the risks inherent in additional handling operations, certain methods envisage using a selective pre-enrichment medium with a lower dose of selective agent(s) than the secondary enrichment medium (in order to preserve the stressed germs). Unfortunately, this decrease in the concentration of selective agent(s) does not fail to affect the selectivity of the overall analysis.

In an attempt to limit this harmful bacterial stress phenomenon, the company Oxoid has developed a system (SPRINT *Salmonella*) which consists of introducing, at the same time as the pre-enrichment medium, capsules containing the selective agent of interest. These capsules were prepared so as to release their contents at the end of 6 h of incubation, so as to leave the stressed target germs sufficient time to strengthen and therefore withstand the contribution of this selective agent. However, this principle does not function optimally, in all likelihood due to the impossibility of homogenising the reaction medium after release of the active principle.

Further, at the end of incubation and despite the use of selective media, the concentration of target microorganisms remains insufficient in certain cases, and/or the concentration of additional flora remains too substantial to perform effective detection of the target microorganisms. In this configuration, the person skilled in the art generally resorts to sample processing methods aimed at increasing the ratio between the concentration of target microorganisms and the concentration of additional flora. For example, after enrichment, a fraction of the sample (preferably between 1 and 10 mL) is processed by a method of immuno-concentration using magnetic beads functionalised by antibodies specific to the target microorganisms. The product of this treatment is then analysed via a detection method, preferably of the molecular biology type, rendering the detection method more specific and more sensitive. This sample processing method is laborious because it is completely manual, and furthermore presents a risk of contaminating the user because the sample, which potentially contains pathogenic agents, is handled after enrichment.

In view of the totality of the problems set out above, one of the objectives of the present invention aims to develop/optimise the incubation time during the biological sample enrichment phase.

Another objective aims to address the disadvantages associated with "conventional" kneading of the biological samples, such as mentioned above. In view of this problem of "conventional" kneading, the invention also aims to make it possible to process several biological samples simultaneously during this step.

The invention also aims to improve the speed of the analysis protocols, comprising placing selective agent(s) or selective medium (media) containing them in contact with a biological sample, whilst not accentuating the microbial stress phenomenon by placing the microorganisms in direct contact with such (a) selective agent(s). This aims to limit—or even prevent—the latency phase in the growth cycle of the sought microorganisms or even, in the worst cases, the total inhibition of their growth.

Another objective of the present invention is to provide a method which makes it possible to increase the rate of sample analysis, and/or to decrease the total time needed to analyse the biological sample.

Another objective of the present invention aims to limit handling of the sample contained in the container, thus limiting the risks of contaminating either the personnel handling the sample or the sample itself. In this regard, the present invention also aims to develop an automated or semi-automated biological sample analysis method.

Another object of the present invention is to provide a method which makes it possible to perform multi-detection.

When a confirmation step is desirable or necessary (cf. above), one of the objectives of the present invention aims to perform the latter continuing on from the detection and/or identification step, preferably within the same container.

Another objective of the present invention is to improve the traceability of the analysis through drastic reduction of the sample handling steps.

The invention also has the objective of improving the gaseous exchanges and in particular the exposure of the target microorganism(s) to the oxygen dissolved within the mixture constituted by the biological sample and at least one culture medium.

The invention also has the objective of producing a dispersion of the microorganisms by impeding the formation of localised colonies or localised masses, in particular of biofilms on the surfaces of the container, but also on the fragments of the sample and within the mixture formed by the biological sample and at least one culture medium.

Another objective of the present invention aims, during the period of incubation/enrichment and growth of the microorganisms, to process the sample (preferably in an automated manner) on the total volume of the sample (and not solely on an aliquot), said processing consisting of immunoconcentrating the target microorganisms (of interest) in order to improve the sensitivity and the specificity of the detection method used post-processing.

Other objectives will become apparent upon reading the present application.

The present invention therefore aims to achieve all or some of the above-mentioned objectives.

STATEMENT OF THE INVENTION

Consequently, the object of the present invention is a method of processing at least one biological sample capable (or suspected) of containing at least one target microorganism, said method being carried out within a container and comprising the following steps:
 a) potentially placing said biological sample in contact with at least one culture medium within said container, the mixture of the biological sample and of said culture medium forming all or part of the contents,
 b) potentially incubating the container at a temperature and for a period of time sufficient to allow the growth of said at least one target microorganism,
 c) performing at least one step of homogenising the biological sample, during which the contents are displaced from a level n, corresponding to the level of the contents at rest, to a homogenisation level $n_h$, distinct from level n, and vice versa,
 said method comprising, before, after or during all or part of the homogenisation step c), preferably after said homogenisation step c), the following step:
 c') generating a displacement of the contents to a level n+1, which is different from the levels n and $n_h$, such that the contents come into contact with at least one culture means and/or at least one analysis means positioned in the chamber of the container, between level n+1 inclusive and level $n_h$ exclusive.

Thus, the method according to the invention makes it possible to efficiently process a biological sample (for the purpose of enrichment and/or analysis) whilst limiting handling of the sample contained in the container, thus limiting the risks of contaminating either the personnel handling the sample or the sample itself. Further, this method can easily be automated in whole or in part and makes it possible to process several biological samples simultaneously.

As mentioned within the preamble of the present application, the above-mentioned steps a) and b)—aimed at enriching the biological sample of interest with target microorganisms—are only necessary when the latter are present in a minimal quantity, for example in the order of several cells in the sample. In this case, the method according to the invention comprises the above-mentioned steps a) and b).

In contrast, when the sample biological of interest is naturally rich in target microorganisms as can notably be the case concerning certain biological samples of food origin (for example cow's milk) or clinical origin (liquid stools sampled from a patient suffering from cholera), the method according to the invention does not require the implementation of steps a) and b).

According to a preferred embodiment, this method of biological sample processing is used within the framework of a method of enriching and/or analysing a biological sample capable of containing at least one target microorganism, said method being carried out within a container and comprising the following steps:
- a) potentially placing said biological sample in contact with at least one culture medium within said container, the mixture of the biological sample and of said culture medium forming all or part of the contents,
- b) potentially incubating the container at a temperature and for a period of time sufficient to allow the growth of said at least one target microorganism,
- c) performing at least one step of homogenising the biological sample, during which the contents are displaced from a level n, corresponding to the level of the contents at rest, to a homogenisation level $n_h$, distinct from level n, and vice versa, said method comprising, before, after or during all or part of the homogenisation step c), the following step:
- c') generating a displacement of the contents to a level n+1, which is different from levels n and $n_h$, such that the contents come into contact with at least one culture means and/or at least one analysis means positioned in the chamber of the container, between level n+1 inclusive and level $n_h$ exclusive.

The above-mentioned step c') notably makes it possible to efficiently process the biological sample of interest (for the purposes of enrichment and/or analysis) whilst limiting the risks of contamination (either of the personnel handling the sample, or of the sample itself).

"Method of enriching a biological sample capable (or suspected) of containing at least one target microorganism" is to be understood, in the terms of the present invention, to be a method intended to allow the growth of at least one target microorganism preferably in the presence of at least one culture medium/enrichment broth (notably when it is suspected that the microorganism(s) sought is/are present in minimal quantity, for example in the order of several cells, in the biological sample), such that said at least one target microorganism is present at the end of the enrichment method at a concentration such that the user may potentially detect it systematically or virtually systematically by resorting to the conventional detection methods (culture on agar media, immunoassays, molecular biology techniques, etc.).

"Method of analysing a biological sample capable (or suspected) of containing at least one target microorganism" is to be understood, within the terms of the present invention, as a method which makes it possible to analyse said target microorganism(s) and/or all or part of their properties. The analysis may notably consist of a method of direct detection—and where applicable of identification—of said microorganism(s) or of a method of indirect detection—and where applicable of identification—for example associated with the detection of nucleotide and/or protein information specific to a type of microorganism to be detected and/or identified. This indirect detection and/or identification may also result from the detection of proteins of bacteriophages specific to said microorganism(s) to be detected. The presence of a target microorganism may also be revealed by a resistance to a given antibiotic or to a set of antibiotics, the resistance profile to this or these antibiotic(s) being, in this case, characteristic of the microorganism(s) to be detected.

This "method of analysing a biological sample capable (or suspected) of containing at least one target microorganism" may also have the goal of determining potential resistance properties of said at least one target microorganism (for example a target bacterial species) to at least one antimicrobial (for example one or more antibiotics).

Further, said "method of analysing a biological sample capable (or suspected) of containing at least one target microorganism" may make it possible to measure one or more biological and/or physico-chemical parameters of said sample, to reveal the presence of a particular contaminant or marker within this sample.

The analysis method according to the present invention also makes it possible to carry out sterility monitoring notably within food and environmental specimens. To do this, we use, as analysis means, generic means of detecting microorganisms such as capture supports functionalised with generic binding partners such as anti-Gram−, anti-Gram+, etc. The type of analysis carried out with the analysis method according to the invention may therefore be not only qualitative (detection and identification of specific microorganism(s)) but also quantitative or semi-quantitative.

According to the present invention, the biological sample may be from various origins, for example of food, environmental, veterinary or clinical origin. Amongst the samples of food origin, non-exhaustive mention can be made of a sample of dairy products (yogurts, cheeses, etc.), meat, fish, egg, fruit, vegetable, water, beverages (milk, fruit juice, soft drink, etc.). Of course, these samples of food origin may also come from sauces or more complex meals, or from non-processed (or partially) processed raw materials. A food sample may finally come from an animal feed, such as oil cakes or animal meals. As examples of biological samples, mention should also be made of the biological samples associated with the environment such as specimens of ground, water, air, etc.

Biological samples of clinical origin may correspond to specimens of biological fluids (whole blood, serum, plasma, urine, cerebrospinal fluid, etc.), of stools, of specimens from the nose, throat, skin, wounds, organs, tissues or isolated cells. This list is obviously not exhaustive.

Generally, the term "sample" refers to a part or a quantity (more particularly a small part or a small quantity) sampled from one or more entities for the purpose of analysis. This sample may potentially have undergone pretreatment, involving for example steps of mixing, dilution or even crushing, in particular if the starting entity is in the solid state.

According to a preferred embodiment, the biological sample to be analysed (namely the biological sample as sampled or having undergone pretreatment, as indicated above) is solid or semi-solid (the molecules present within said biological sample possess relatively high intercohesion).

The biological sample analysed is, in general, capable of containing—or suspected of containing—at least one target microorganism. In the majority of cases, the latter is a pathogenic microorganism (such as *Salmonella*) which should be detected for health purposes.

The term "microorganism" has the same meaning as that generally accepted in microbiology and comprises notably gram positive or gram negative bacteria, yeasts, moulds and more generally, single-cell organisms, invisible to the naked eye, which can be handled and multiplied in a laboratory.

According to a preferred embodiment, the microorganism(s) to be detected are bacteria, for example enterobacteria such as *E. coli*.

If the microorganism enrichment of a biological sample is carried out with a view to detecting and, where applicable, identifying one or more target microorganisms, this detection—and where applicable identification—may be performed directly (through contact of the microorganisms with a capture support exhibiting a very good affinity for the latter) or indirectly (for example by the detection of proteins secreted by the target microorganisms). By way of illustration, it is possible to cite the detection of the toxins secreted by *Staphylococcus aureus*.

Advantageously, the biological sample is placed in contact with at least one culture medium enabling the growth of the microorganisms and, in particular, of the target microorganism(s). "Culture medium", is to be understood to be a medium comprising all the elements necessary for the survival and/or for the growth of the microorganisms and, in particular, of the microorganisms sought (for example buffered peptone water). The culture medium may contain any additives, for example: peptones, one or more growth factors, carbohydrates, one or more selective agents, buffers, one or more gelling agents, one or more vitamins, etc. This culture medium may present itself in liquid or gel form ready for use, namely ready to be seeded in a tube, in a flask or on a Petri dish. The expression "culture medium" very obviously encompasses enrichment media and broths.

The container used for the purposes of the present invention is an open or (for example hermetically or tightly) sealed chamber potentially equipped with a vent system, preferably sealed (potentially equipped with a vent system), within which the biological sample of interest and one or more culture media are placed in contact.

According to one particularly preferred embodiment, the container is a vessel comprising a base and walls. It may be, for example, a rigid container such as a flask, a bottle or a pill box. According to a preferred embodiment, the container is a bag possessing a flexible shell, of the homogenisation bag type. Preferably, at least one wall of the container is transparent so as to be able to discern the volume occupied by the liquid inside the container.

The contents made up of the mixture comprising the biological sample and potentially at least one culture medium may, of course, comprise additional elements, such as vitamins or other nutrients useful for the culturing of microorganisms, selective agents, specific substrates and other elements well known to the person skilled in the art.

However, the method according to the present invention requires that these contents be mobile, notably to allow homogenisation under slight agitation. Preferably, these contents are a fluid, advantageously a liquid.

Concerning the incubation step b), when the method according to the invention comprises this step, the person skilled in the art will be able, from his experience, from his general knowledge and/or from the bibliographic data available to him, to adapt the temperature and the period of time necessary to enable a sufficient growth of the target microorganism, depending on the type of microorganism sought. For information and as mentioned in the preamble of the present application, the incubation generally takes place at a temperature ranging from 25 to 45° C. for a predetermined period of time (for example from 6 h to 48 h).

Preferably, contrary to the conventional kneading carried out with the aid of kneading apparatus of the Stomacher® type, mixers and other Pulsifiers®, the homogenisation of the biological sample is carried out, according to the present invention, less violently than the prior art kneading and for a longer period of time, notably so as to prevent excessive deterioration of the sample matrix (capable of causing interference on a detection means), as well as the potential risks of perforating the pouch of the homogenisation bag. This proves to be particularly advantageous within the framework of processing a biological sample with a relatively firm consistency, for example solid or semi-solid.

Preferably, during this homogenisation step (called "soft homogenisation"), the volume displaced from level n (level of the contents at rest) to level $n_h$ (homogenisation level) is less than or equal to 50%, advantageously less than or equal to 40%, preferably less than or equal to 30%, and the frequency of the displacement of the contents is less than or equal to 2 Hertz (Hz), preferably less than 2 Hz, preferably of between 0.1 and 1 Hz, advantageously of between 0.45 and 0.7 Hz. By way of comparison, the Stomacher® kneader causes, during the kneading step, a displacement of the volume of the contents in excess of 100% and kneads at a frequency ranging from 2 to 5 Hz, generally of between 3 and 4 Hz.

Generally, and at a biological sample breakdown pressure equivalent to that of the prior art kneaders, the homogenisation is carried out at the aforementioned frequency, namely less than or equal to 2 Hz, preferably less than 2 Hz, preferably of between 0.1 and 1 Hz, advantageously of between 0.45 and 0.7 Hz. By way of example, at breakdown pressure equal to Stomacher® kneaders which are commercially available (variable between 3 and 30 kilograms on the pouch containing the food sample), and considering a conventional homogenisation pouch (or bag) of which the wall is made of flexible plastic (for example PVC, polyethylene or polyester), the frequency is as indicated previously, namely less than or equal to 2 Hz, preferably less than 2 Hz, preferably of between 0.1 and 1 Hz, advantageously of between 0.45 and 0.7 Hz.

According to a particular embodiment, at least two steps of homogenisation of the biological sample may be performed, namely a first step intended for dispersing the analysed biological sample (for example of food origin), generally of a duration of between 2 and 90 minutes, preferably between 10 and 60 minutes, advantageously between 15 and 50 minutes, then a second homogenisation step able to continue until the end of the incubation period, this second homogenisation step making it possible to obtain good oxygenation of the medium as well as an ad hoc dispersion of the microorganisms (notably bacteria) in the medium, so as to prevent the interactions with the biological (for example food) particles from the biological (for example food) sample. This second homogenisation step may continue subsequent to the end of the incubation step.

Specifically, and when a device with blades (or with arms) is used, said blades compressing a homogenisation pouch with flexible walls (for example made of a plastic material of the PVC, polyethylene or polyester type), the homogenisation bag is compressed by at least one blade at the aforementioned frequency, namely less than or equal to 2 Hz, preferably less than 2 Hz, preferably of between 0.1 and 1 Hz, advantageously of between 0.45 and 0.7 Hz with a blade travel distance expressed in centimeters adjustable from 0.1 to 2.7 cm, preferably of 2.3 cm leaving a clearance of 0.4 cm between the blades and the fixed wall against which the homogenisation pouch is compressed.

This homogenisation of the biological sample, which can be referred to as "soft" homogenisation compared to the "violent" kneading from the prior art, makes it possible to overcome all or part of the problems inherent in the prior art kneading devices.

"Culture means" is to be understood, in the terms of the present invention, to be a means for promoting and/or orienting the culture of the target/sought microorganism(s). This culture means may be, for example, a selective agent, such as one or more antibiotic(s), intended for improving the selectivity of the analysis (by eliminating all or part of the undesired microorganisms).

The culture means may also be a nutrient, for example selected from amongst vitamins, peptones, carbohydrates, etc., intended for promoting the primary function of enriching the tested biological sample with target microorganisms.

"Analysis means" is to be understood as any means making it possible to directly or indirectly measure (in association with at least one other analysis means) one or more biological and/or physicochemical parameters of a biological sample (for example pH variation), to reveal the presence of a contaminant or of a particular marker in said sample. Preferably, such an analysis means enables direct or indirect analysis of the target microorganism(s), as well as of all or part of their properties and any change of the medium generated by said microorganism(s) (such as a change of pH). A means enabling indirect analysis (also referred to as "indirect analysis means") may, for example, consist of an indicator, marker or other tracer which will be the subject of one or more later analyses, or also of a concentration means such as an immunoconcentration means. In the latter case, the function of the concentration means is to ensure that the analyte or analytes sought is/are in a sufficient concentration for the purposes of the later analysis steps (carried out in situ or ex situ).

Preferably, the analysis means consist of one or more means of detecting microorganisms—directly or indirectly (in association with at least one other detection means). In other words, the detection means used may be any means which makes it possible to detect, directly or indirectly (in association with at least one other detection means), the presence or the absence of target microorganisms in a biological sample and making it possible, where applicable, to identify them directly or indirectly.

In a non-limiting manner, the aforementioned detection means may be selected from amongst electrical (notably electrochemical) detection means, optical detection means, acoustic detection means, thermal detection means, mechanical detection means, and magnetic detection means.

One example of useable detection means according to the present invention consists of a capture support functionalised/sensitised by a binding partner specific or non-specific (preferably specific) to a target microorganism. According to a preferred embodiment, the specific binding partner is selected from the group comprising antibodies, Fab fragments, Fab' fragments, recombinant or non-recombinant phage proteins, phages or any other ligand well known to the person skilled in the art. The revelation of the presence of the target microorganisms on the capture support may be performed via any appropriate revelation system, i.e. enabling the detection of the target microorganism(s). "Revelation system" is to be understood to be any molecule capable of binding with the microorganisms or the binding partners of said microorganisms and making it possible, through their transduction properties (fluorescence, coloration, radioactivity, etc.), to reveal the presence of said microorganisms. This revelation of the presence of the target microorganisms may be notably obtained by visualisation (to the naked eye) or optical reading (via a camera-type optical reading device) of a coloration (such as a red coloration due to the reduction of TTC to formazan by the microorganisms) or of a fluorescence on all or part of the capture support.

It is important to note that said at least one culture means and/or said at least one analysis means is/are placed inside the container so as to:
  not be in contact with the contents when the latter are at level n or are displaced from this level n to level $n_h$, and come into contact with the contents during the level variation (preferably elevation) step c').

According to a particular embodiment, instead of a culture means or an analysis means, a culture and analysis means are used.

The displacement of the contents may be obtained by any means known to the person skilled in the art. In particular, this displacement may be generated by the application of a force or a set of forces onto the container, or also by changing the balance of forces applied to the container (for example if the container is held at two points by two retaining forces and if one of the two forces ceases, the container will tilt and the level of the contents will vary, on at least a part of the inner surface of the container, from the rest level to a level situated above the latter, and will possibly come into contact with the culture means and/or the analysis means).

Another embodiment which makes it possible to obtain a variation of the level of the contents inside the container may be observed when the container is positioned on a plate agitator (commonly referred to as a "tilting floor"), the latter causing the level of the contents inside the container to vary regularly, in a back and forth motion (comparable to a pounding and recoiling motion).

The displacement of the contents may also be obtained by applying a force or a system of forces to the interior of the container, for example by inflating and deflating an inflatable flexible pouch (such as a balloon or an inflatable ring) placed in the chamber of the container.

If the upper part of the container is considered as being the "top" part and the lower part of this container as being the "bottom" part, the level of the contents will very slightly rise during the homogenisation step c) to a homogenisation level $n_h$ but not sufficiently to come into contact with the culture means and/or the analysis means positioned in the chamber of the container, above level $n_h$. When a culture means of the selective agent type is used, this is definitely desirable as indicated previously, in order to not place this selective agent in contact with the biological sample at too early a stage, namely before the target microorganisms have overcome the microbial stress phenomenon and are sufficiently "viable" to support the input of this selective agent.

When a detection means is used as an analysis means, this is also definitely desirable, in order to preserve the integrity of the detection means before the detection/identification step has taken place. This is particularly true in the case of a biosensor, so as to prevent a deterioration of the biosensor's abilities due to the non-specific compounds contained in the sample (in particular subsequent to the homogenisation step).

Roughly, the method according to the invention makes it possible to raise, precisely and at will, the level of the contents (preferably in the liquid state) in the container. This function enables differentiated recovery of a reagent (for example of an antibiotic-type selective agent) and its homogenisation in the contents, thus ensuring its optimal efficacy. This makes it possible to resolve a major problem in terms of selectivity.

According to a preferred embodiment, the container is a pouch made of flexible or semi-flexible material (of the analysis pouch or homogenisation pouch type) and the rise of the liquid within the latter is obtained via a system of pressure and depression applied to the pouch by a mechanical means, preferably by the motion of arms or blades.

It is definitely possible—and in certain cases desirable—to set up a new homogenisation step subsequent to step c') (as indicated supra), for example so as to homogenise the contents comprising the biological sample, the culture medium and the culture means recovered following the level elevation carried out at step c'), within the container.

According to a preferred embodiment, said level n+1 is situated above the homogenisation level $n_h$, which level $n_h$ is situated above the rest level n, such that the "level variation" step c') is, preferably, a "level elevation" step, during which the contents rise from level n or $n_h$ to the higher level n+1 so as to come into contact with at least one culture means and/or at least one analysis means positioned in the chamber of the container above the homogenisation level $n_h$ and below level n+1 or at the same height as the latter. Thus, during variations of the level of the contents occurring during the homogenisation step (from level n to level $n_h$ and vice versa), said at least one culture means and/or at least one analysis means is in a manner of speaking "preserved", which signifies that it does not come into contact with the contents during a homogenisation step. In other words, this prevents said culture means and/or said analysis means from being "polluted/damaged" during a homogenisation step.

According to a preferred embodiment, the displacement of the contents from level n to level $n_h$ and the displacement of the contents from level n to level n+1 are generated by the same displacement means, at two different intensities, preferably, the intensity of the displacement is greater for displacement to level n+1 than to level $n_h$. This allows easy development, at lower cost, of a method making it possible to perform both at least one homogenisation step and at least one so-called "level variation" step, (preferably "level elevation" step), in order to recover at least one culture means and/or at least one analysis means, during the incubation step or subsequent to it.

According to a particular embodiment, said method according to the invention comprises, subsequent to step c'), at least the following step:

c") generating a displacement of the contents to a level n+1+x, such that the contents come into contact with at least one additional culture means and/or at least one additional analysis means positioned in the chamber of the container, between levels n+1+x inclusive and level (n+1+x)−1 exclusive, wherein x is a whole number, preferably between 1 and 10.

Preferably, step c') and/or step c") (preferably both) is/are performed during the incubation step b). According to a particular embodiment, at least one homogenisation step is performed after step c') and/or after step c").

This embodiment makes it possible to perform several steps of culture means enrichment and/or several analysis steps (for example of direct or indirect detection) at different levels of the container.

Preferably level n+1+x is situated above level (n+1+x)−1.

By way of example, if x represents the whole number 1, step c") consists in generating the displacement of the contents to a level n+2, distinct from levels n, $n_h$, and n+1 (preferably situated above the latter), so as to come into contact with a culture means and/or an analysis means positioned within the container, between level n+1 (inclusive) and n (exclusive). Thus, according to this example, a selective agent may for example be positioned between level n (exclusive) and level n+1 (inclusive) and a detection means such as a biosensor between level n+1 (exclusive) and level n+2 (inclusive). Firstly, step c') makes it possible to recover the selective agent in the contents comprising the biological sample (or its residues) and at least one culture medium. Optionally, a homogenisation step may be carried out subsequent to step c'), so as to optimise the efficacy of the selective agent. When the selectivity level is considered as being sufficient, step c") is performed in order to detect and, where applicable, identify the target microorganisms having survived the selective agent.

The method according to the invention may incorporate as desired, depending on the user's wishes, various culture and/or analysis means which can be positioned within the container, between levels n+1+x (inclusive) (n+1+x)−1 (exclusive). Further, no handling is required between the various steps. This method is consequently very easily automatable.

According to a preferred embodiment, the method according to the invention comprises a step consisting of generating the displacement of the contents to a transfer level $n_t$, such that the transfer of all or part of said contents proceeds from this transfer level $n_t$ of the container to another part of said container or to at least one other container.

This transfer of all or part of the contents may prove to be significant notably with regard to detection—and potentially identification—of the target microorganism(s) "deported" to another container, this other container possibly being an analysis device, for example a VIDAS®. According to an alternative, this transfer makes it possible to perform—either in another part of the same container, or in another container—additional enrichment steps, if the case in question justifies it.

According to a particularly preferred embodiment, the homogenisation step c) is carried out at least in part during the incubation step b), preferably during a period of time greater than 2 minutes. Thus, the homogenisation step c) may for example:

commence before the start of the incubation step b) and continue during all or part of the latter; or commence during incubation step b) and continue during all or part of the latter; or commence before the start of the incubation step b) or during incubation step b) and continue after the end of said incubation step b).

In any event, this embodiment is particularly advantageous since it makes it possible to harness all or part of the incubation time generally "lost" in the methods of the prior art.

According to a particular embodiment, the homogenisation step c) commences before the launch of the incubation step in order to allow a sampling of an aliquot after homogenisation and before incubation to carry out, for example, a counting of microorganisms.

According to another particular embodiment, the homogenisation step c) commences concomitantly with the incubation step b) or in the first minutes following the start of incubation step b), preferably within a period of time of between 1 and 10 minutes starting from the beginning of said incubation step b).

The fact that the homogenisation step c) commences concomitantly with the incubation step b), or within the first minutes following the start of the incubation b), by no means represents an arbitrary parameter since, on the contrary, and against all expectation, the latter has made it possible to obtain the best results in terms of enrichment of the tested biological sample whilst attenuating the background noise generated during a conventional homogenisation.

Another object of the invention relates to a method of enriching at least one biological sample capable of containing at least one target microorganism, said method implementing the biological sample processing method according to the invention, wherein said at least one culture means and/or at least one analysis means is a culture means such as an antimicrobial-type selective agent.

The invention also relates to a method of analysing at least one biological sample capable of containing at least one target microorganism, said method implementing the method of processing at least one biological sample according to the invention, said at least one culture means and/or at least one analysis means being at least an analysis means such as a functionalised capture support or a biosensor, and said method comprising a supplementary step d) consisting of analysing said at least one biological sample, preferably of analysing (directly or indirectly) said at least one target microorganism, with the aid of said analysis means.

Advantageously, this analysis method comprises, before and/or after the analysis step d) (preferably before the latter), at least one step of transferring all or part of the mixture comprising said biological sample, potentially the culture medium, said at least one analysis means, from the container, then called the main container, to a second container called the secondary container. According to a preferred embodiment, said method comprises, before and/or after the analysis step d) (preferably before the latter) the transfer of the analysis means to said secondary container (consisting, for example, of a VIDAS® analysis device).

According to a preferred embodiment, the aforementioned analysis method comprises, subsequent to analysis step d), a confirmation step e) aiming to confirm or overturn the analysis results obtained at the end of the analysis step d). This confirmation step may be carried out either in situ, namely in the chamber of the above-mentioned main container, or ex situ, namely for example within the aforementioned secondary container (such as a VIDAS® analysis device).

Another object of the present invention concerns a method of enriching a biological sample capable of containing at least one target microorganism, said method being carried out within a container and comprising the following steps:

a) placing said biological sample in contact with at least one culture medium within said container, the mixture of the biological sample and of said culture medium forming all or part of the contents,
b) incubating the container at a temperature and for a period of time sufficient to allow the growth of said at least one target microorganism,
c) carrying out homogenisation of the biological sample during at least a part of the incubation step b), preferably for a period of time greater than 2 minutes. Advantageously, during this step c), the volume displaced from the level of the contents at rest n to the homogenisation level $n_h$ is less than or equal to 50%, advantageously less than or equal to 40%, preferably less than or equal to 30%, and the frequency of the displacement of the contents, during said homogenisation step c), is less than or equal to 2 Hz, preferably less than 2 Hz, preferably of between 0.1 and 1 Hz, advantageously of between 0.45 and 0.7 Hz.

The fact that the applicant has discovered, surprisingly, that a homogenisation step (which can be referred to as "soft" homogenisation, cf. definition set out supra) could be performed during all or part of the incubation step b) (for example at the start of incubation) makes it possible, in addition to obtaining good oxygenation of the medium, to provide nutrients of the target microorganism(s), etc., to obtain a biological sample less altered than a violently "kneaded" biological sample, according to the conventional methods of the prior art. This notably makes it possible to prevent in fine the risks of interference of the matrix residues resulting from the destruction of the biological sample at the means used in detection (this is particularly true for the detection means used in molecular biology, such as PCR probes). Generally, a clearer supernatant is obtained, with fewer particles in suspension, and therefore less background noise. Furthermore, the device implemented in this method proves to be considerably less noisy than those used in the prior art.

According to a particularly preferred embodiment, the object of the invention is also a method of analysing at least one target microorganism, said method implementing the enrichment method according to the invention, said method comprising, subsequent to step c), an analysis step d) with the aid of at least one analysis means (for example a step of identifying microorganism(s) via at least one detection means such as a capture support functionalised by a binding partner), said analysis step being carried out within the container or outside of it.

Preferably, the analysis method is a method of detection—and where applicable of identification—comprising, subsequent to step c) a step of detection d) with the aid of a detection means, said detection step being carried out within the container or outside this.

Preferably, the aforementioned detection—and where applicable identification—step is carried out within the container (in the chamber of the latter), for the sake of practicality and above all with a view to automation.

In the event of the detection of the microorganism(s) sought being carried out in the container, the latter may comprise, inside it, any revelation system enabling the detection of the presence of this or these microorganism(s) and, where applicable, their identification.

Revelation system is understood to be any molecule capable of binding with the microorganisms or the binding partners of said microorganisms and making it possible, through their transduction properties (fluorescence, coloration, and radioactivity notably), to reveal the presence of said microorganisms.

According to a preferred embodiment, the revelation system is based on the reduction of certain tetrazolium salts by the microorganisms, in particular of 2,3,5-triphenyl tetrazolium chloride (which has the acronym TTC) by the microorganisms. Simultaneously to the growth, the TTC (colourless in its non-reduced form) is internalised by said microorganisms, then reduced by the latter into triphenylformazan (red in colour), thus colouring said microorganisms red and then enabling their revelation on a capture support, preferably positioned within the container. The direct and real-time detection of microorganisms in a food sample, during the incubation period, is, in this case, performed by automated or non-automated optical reading of the capture support, preferably automated thanks to an optical detection device.

Advantageously, at least one binding partner, specific or non-specific, of the microorganism(s) is fixed onto a capture support. A capture support may be any support enabling the revelation of microorganisms. In this regard, it is advisable to cite particular supports, which are potentially magnetic, or even monoblock supports, which are potentially porous. The capture support may simply be an inert support, such as a plastic or fibre-glass plate or, advantageously, may be sensitised with a potentially specific binding partner. The capture support may also consist of a compressible monoblock support. According to a particular embodiment, the capture support may be as one with the detection means. This is the case, for example, when the capture support is constituted by one electrochemical biosensor or an optical fibre.

Concerning the binding partner, when such a binding partner is fixed onto a capture support, it is advantageously selected from antibodies, Fab fragments, Fab' fragments, recombinant or non-recombinant phage proteins, phages, lectins, aptamer-type nucleic acids or any other ligand well known to the person skilled in the art.

Advantageously, the detection means, preferably present in the chamber of the container is chosen from the group constituted by: electrical and notably electrochemical detection means, optical detection means, acoustic detection means, thermal detection means, mechanical detection means, magnetic detection means (non-exhaustive list) or a combination thereof.

When the detection of the target microorganism(s) is performed in the container chamber itself, and according to a particular embodiment, it is definitely possible to envisage coupling the detection means in order to carry out the detection, on the one hand, and, on the other hand, to perform simultaneously or subsequently the confirmation, if the latter is desired or necessary (which is generally the case in the agrifood field). For example, it is possible to carry out the detection of the target microorganism(s) by means of an electrochemical biosensor. If the fixation of the target microorganisms is performed by means of specific binding partners, the detection step therefore constitutes an identification step. An optical analysis of the microorganisms specifically fixed onto the biosensor in the analysis zone by an optical detection device therefore makes it possible to confirm the identification of the microorganisms. If the optical detection device is a Raman spectrometer, an analysis of the Raman spectrum by comparison with a database of reference spectra corresponding to the various target microorganisms, then makes it possible to confirm the identification of said microorganism.

According to another particular embodiment, it is possible to carry out the detection and the confirmation with the same technology. Thus, if the detection means is an optical means such as a means of measuring intrinsic fluorescence, it is particularly advantageous to carry out the detection of the target microorganisms by the appearance of intrinsic fluorescence and potentially their identification. The response is therefore a yes (fluorescence present)/no (fluorescence absent) response. If there is fluorescence, then a spectral analysis of the fluorescence signal by comparison with a database of reference spectra corresponding to the various target microorganisms therefore makes it possible to identify said microorganism and, as a result, confirm the detection of the presence of said microorganism.

Preferentially, the detection of the microorganism(s) is carried out in real time. Nevertheless, alternatively, the detection of the microorganism(s) may be carried out, at the end point, at the end of the growth step of said microorganism(s).

According to a particular embodiment, the detection means present within the container is connected to a data analysis system.

Advantageously, the connection between the detection means and the data analysis device is a wire connection or a wireless connection.

According to a particular embodiment, the detection means used, preferably within the vessel, is an electrochemical biosensor for the detection of at least one microorganism present in the biological sample placed within the container. This biosensor comprises a support including:
  at least one detection electrode, coated with at least one electroactive polymer, on which is fixed, by one of its ends, at least one single-strand or double-strand oligonucleotide, the second end of said oligonucleotide being bound to at least one specific or non-specific binding partner of the microorganism(s) to be detected;
  at least one counter-electrode.

Advantageously, the electroactive polymer is taken from the group comprising polypyrrole, polyacethylene, polyazine, poly(p-phenylene), poly(p-phenylene vinylene), polypyrene, polythiophene, polyfuran, polyselenophene, polypyridazine, polycarabazole, polyalinine.

According to a particular embodiment, the electroactive polymer includes at least one electrochemical mediator. Such an electrochemical mediator is taken from the group comprising ferrocene, quinone and the derivatives thereof or any other mediator well known to the person skilled in the art.

According to an alternative embodiment, the electrochemical mediator finds itself in free form in the culture medium. Such a mediator may be for example the ferricyanide/ferrocyanide pair $[Fe(CN)6]^{3-}/^{4-}$, the iridium chloride pair $[[IrCl_6]^{3-}/^{4-}$ or ruthenium hexamine $[Ru(NH_3)_6]^{3+}/^{2+}$.

Preferentially, the bond between the oligonucleotide and the binding partner of the microorganism(s) is made by means of at least one biotin-streptavidin or biotin-avidin binding pair.

When the oligonucleotide is single-strand, a biotin is fixed onto the 3' end of said nucleotide, the 5' end allowing the fixation of the latter onto the electroactive polymer, notably by covalent bonding. By using a binding partner which is also biotinylated, it is then easy to fix this to the 3' end of the oligonucleotide by means of a streptavidin or avidin molecule.

When the oligonucleotide is double-strand, the first strand is fixed, notably by covalent bonding to the electroactive polymer by its 5' end. The second strand, for its part, is biotinylated at its 5' end, allowing the fixation of the binding partner which is also biotinylated, by means of a streptavidin or avidin molecule.

Advantageously, the binding partner is taken from the group comprising: antibodies, Fab fragments, Fab' fragments, recombinant or non-recombinant phage proteins, whole phages or bacteriophage fragments.

Thus, the method according to the present invention may comprise a supplementary step of detecting microorganisms or the protein secreted by the latter via the binding partner.

According to another particular embodiment, the revelation system is a non-specific substrate internalised by the microorganism(s) to be detected. Thus, once a certain quantity of colored target microorganisms has been effectively captured (in a positive sample case), a change of the optical properties of the capture support (consisting generally of a solid phase, for example of a compressible, potentially porous, support as indicated previously) takes place by the appearance of coloration (for example a red coloration in the case of TTC) thereon (transduction of the biological signal). This coloration of the capture support is therefore detectable to the naked eye or measurable via the use of a reading machine such as a camera. To facilitate reading, it is preferable that the capture support is no longer in contact with the culture medium.

According to another embodiment, the revelation system is cellular staining of the microorganism(s) to be detected. The detection step may be carried out with the aid of a means chosen from optical detection means, magnetic detection means, electrochemical detection means, electrical detection means, acoustic detection means, thermal detection means or a combination thereof.

Another object of the present invention concerns a device allowing the implementation of the method according to the invention, said device comprising at least one site for receiving at least one container, at least one displacement means for generating the displacement of the contents, wherein the displacement means is capable of/suitable for generating at least two displacements of the contents at at least two different intensities, the weakest displacement intensity allowing the homogenisation of the biological sample and the strongest displacement intensity allowing the generation of a displacement of the contents such that this comes into contact with at least one culture means and/or at least one analysis means. In other words, said at least one container comprises, within it, at least one culture means and/or at least one analysis means placed so as to:

not be in contact with the contents when the latter are at level n or are displaced from this level n to the level $n_h$, and come into contact with the contents during the level variation (preferably elevation) step c').

As indicated previously, the use of a displacement means capable of/suitable for generating at least two displacements of the contents at said at least two different intensities enables the easy development, at lower cost, of a device making it possible to perform both at least one homogenisation step and at least one so-called "level variation" step (preferably "level elevation" step), in order to allow the contents to come into contact with at least one culture means and/or at least one analysis means, during the incubation step or subsequent to it.

According to an advantageous embodiment, said device comprises:

Preferably, the device comprises at least two sites in order to process several containers simultaneously.

This device may be considered to be an improved carrier capable not only of receiving one—and preferably several—containers but also of acting on this or these container(s), by generating for example a homogenisation of its/their contents or a level elevation so as to place the contents in contact with a culture means and/or an analysis means.

According to a particular embodiment, the container may be a vessel comprising a base and walls. According to this embodiment, a force or a set of forces may be applied onto at least one wall and/or the base of the vessel by the displacement means.

According to a particularly preferred embodiment, the container comprises at least one flexible or semi-flexible wall. Preferably, this flexible or semi-flexible wall is made of a translucent or transparent material, advantageously transparent.

Advantageously, the container is of the bag or flexible pouch type (such as a homogenisation pouch or bag), constituted in full or in part by a pliable (or deformable) membrane. Thus the device displacement means will act on this pliable membrane—for example by pressure—in order to deform it and thus bring about the elevation of the level of its contents to a predefined level, for example a homogenisation level $n_h$ or a higher level (for example level n+1) in order to place the contents in contact with a culture and/or detection means positioned in the container, between levels $n_h$ and n+1.

Preferably, the device comprises an optical detection means which makes it possible to detect the presence of said target microorganism.

This makes it possible to move towards automation of the method according to the invention. This optical detection means may be a camera or a photographic apparatus. It may also comprise advanced functionalities such as, for example, reading optical density (OD) or fluorescence.

Still with a view to enabling the easy automation of the method according to the invention, a preferred embodiment of said invention concerns a device comprising a control means which makes it possible to alter the intensity of displacement of the contents, for example by adjusting the intensity and/or the frequency of the force, or of the set of forces, applied to the container in order to generate the displacement of the contents (for example to the homogenisation level $n_h$ and/or to a higher level such as level n+1). This integrated control means may, advantageously, ensure the management and the coordination of the other means of the device, namely notably of the optical detection means and/or of the heating means.

The object of the invention is also the use of the aforementioned device for implementing the method according to the invention.

In order to enable the incubation of the contents (step b) of the method), the device may either be placed in a conventional incubator, suitable for the occasion, or comprise at least one heating means which enables the incubation step b) (for example a heating means by contact) to be carried out. This option is particularly preferred because it avoids a handling step, namely the transport of the device to and in the incubator.

Furthermore, the integration of this heating function is particularly beneficial since it enables the media heating speed to be increased to very rapidly reach the optimal temperature for growth of the microorganisms, thereby the latency phase to be decreased.

Furthermore, the integration of the heating means into the device of the invention offers a supplementary advantage in that it permits temperature variations during the incubation and potentially thus makes it possible to gain selectivity and/or detection sensitivity. By way of example, mention should be made of the ELISA method for the detection of *Listeria* spp, based on the use of anti-flagellar antibodies. Indeed, the optimal temperature for growth of *Listeria* spp is greater than 35° C., whereas the optimal temperature for the production of flagella is 30° C. One solution consists therefore in promoting the growth of the microorganism by incubating the sample at a temperature greater than 35° C., usually 37° C. initially, and then in promoting the production of flagella by lowering the temperature to 30° C., which is permitted by the device according to the invention in its version which integrates at least one heating means. These thermal variations may be repeated several times, be progressive or rapid, and follow or not follow a non-linear evolution. These thermal variations may accompany a modification of the height of culture medium obtained according to the methods described above.

Thus, the possibility of automatically modifying the temperature conditions during the incubation step b) offers a real advantage.

The invention also concerns a carrier which makes it possible to incubate and homogenise the contents of at least one container, said contents being formed by the mixture of a biological sample and at least one culture medium intended for promoting the growth of the microorganisms present within said biological sample, said carrier comprising at least one—and preferably at least two—site(s) for receiving said at least one container and at least one homogenisation means for homogenising said contents, said carrier being suitable for receiving at least one container comprising at least one wall made of pliable material and said at least one homogenisation means comprising at least one applicator suitable for exerting a force on said at least one wall made of pliable material in order to enable the deformation of said wall made of pliable material to modify the form of said at least one container so as to homogenise the contents.

Preferably, the applicator is suitable for exerting, periodically, a force on the pliable wall of the container (consisting of a vessel, for example).

Preferably, the applicator is connected to a management/control element which makes it possible to adjust/manage the intensity of the force exerted onto the vessel wall, made of pliable material, and the frequency with which said force is applied.

According to a particular embodiment, the site for receiving the container is delimited by at least a first and a second support element, suitable for coming into contact with the opposite sides of the container, wherein at least the first support element is movable relative to the second support element in order to modify the distance between the first and the second support elements in order to modify the force exerted onto the container wall, made of pliable material.

According to a preferred embodiment, the site for receiving a container is delimited by at least one first and second movable arms, suitable for coming into contact with a first side of the container and at least one fixed support element suitable for coming into contact with a second side of the container; said at least one first and second movable arms being suitable for exerting a force so as to push said container against said at least one fixed support element.

According to a preferred embodiment, said at least one first and second movable arms are suitable for displacing alternately.

According to another preferred embodiment, said at least one first and one second movable arms are suitable for moving together. According to this preferred embodiment, the fact that the movable arms move together makes it possible to generate an "elevation of level" of the contents to a level n+1, situated above the homogenisation level $n_h$.

According to a particularly preferred embodiment, said at least one first and second movable arms are suitable for moving alternately or together. Preferably, and still according to this particularly preferred embodiment, if it is desired to carry out (soft) homogenisation of the contents, an alternate displacement of said at least one first and second movable arms is generated—advantageously via the control means—preferably at a frequency less than or equal to 2 Hz, preferably less than 2 Hz, preferably of between 0.1 and 1 Hz, advantageously between 0.45 and 0.7 Hz. Nonetheless, when it is desired to induce an "elevation of level" of the contents to a level n+1, situated above the homogenisation level $n_h$, a joint (simultaneous) displacement—advantageously via the control means—of said at least one first and one second movable arms is preferably generated.

The object of the invention is also the use of the aforementioned carrier for implementing the method according to the invention.

According to a particular embodiment, the device according to the invention comprises an opening and closing means of the container (for example a means of opening and closing the sealed pouch). Preferably, within the framework of an automated method, this means of opening and closing the container is controlled by the aforementioned control means.

The object of the invention is also the use of the aforementioned device for implementing the method according to the invention.

Another object of the invention concerns an incubator suitable for incubating at least one biological sample capable of containing at least one target microorganism at a temperature and for a period of time sufficient to enable the growth of the target microorganisms, said incubator comprising the device according to the invention.

BRIEF DESCRIPTION OF THE DRAWINGS

The invention, its functionality, its applications and its advantages shall be better understood by reading the present description, made with reference to the figures, in which.

DETAILED DESCRIPTION OF THE INVENTION

The detailed description below aims to set out the invention in a manner which is sufficiently clear and complete, notably by means of examples and references to figures, but must by no means be regarded as limiting the scope of protection to the particular embodiments which are the subject of said examples and figures.

Figure 1:
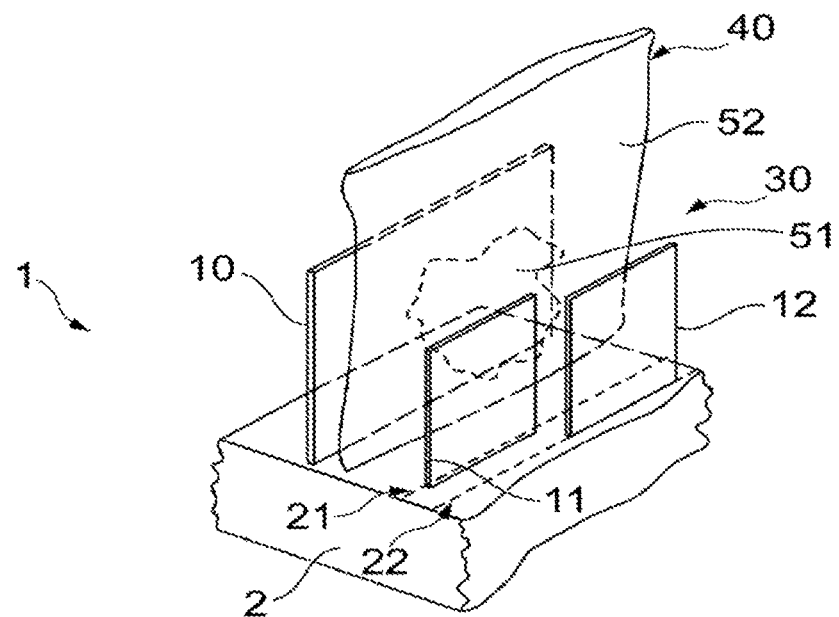
FIG. 1 depicts a perspective view of a device according to the invention (improved "carrier"), suitable for incubating the contents of a container.

For the purposes of clarity, FIG. 1 depicts only a part of a device 1 according to the invention. The device 1 is equipped with a base 2 onto which a wall 10 has been fixed. The wall 10, according to the embodiment from FIG. 1, comprises a wall with a fixed position relative to the base 2.

Furthermore, the device 1 comprises a first and a second movable arm (similar to two blades) 11 and 12, which are movable in relation to the base 2. The movement of said arms 11 and 12 relative to the base 2 may be generated by any suitable means, such as an electric motor.

The movable arms 11 and 12 may be displaced from a first position, indicated using the line 22, to a second position, indicated using the line 21. According to this FIG. 1, the arm 11 is in the second position 21 and the arm 12 is in the first position 22.

The arms 11 and 12 are movable in order to be able to exert a pressure onto the outer surface of a container 40 positioned within the device 1, in a site 30 envisaged for this purpose. This site 30 is delimited on one side by the fixed wall 10 and on the other by the set of arms 11 and 12. This container 40 may be of the Stomacher® bag type. The container 40, such as shown in FIG. 1, comprises a bag made of flexible material able to receive, inside it, contents comprising or consisting of the assembly of a sample 51 (depicted in the drawing much larger than in reality) and a culture medium 52. This culture medium 52 is, for example, in the liquid state.

The biological sample 51 may be the whole sample for which the user wishes to monitor the presence of microorganisms of interest. As indicated previously, the sample may be of food, environmental or clinical origin (non-exhaustive list) and the microorganisms sought may be pathogenic microorganisms, for example *Salmonella* or *E. coli*.

The culture medium 52, present inside the container 40 aims to ensure the enrichment of the biological sample with target/sought microorganism(s). In other words, the culture medium 52 offers the microorganisms sought the ideal conditions which make it possible, if they are present, to grow inside this container 40. Of course, as is known to the person skilled in the art, the culture medium or media used may vary depending on the microorganisms sought.

When the container 40 is positioned in the site 30, the assembly formed by the device 1 and the container 40 may, for example, be placed in incubation inside an incubator (not depicted). These conditions may be optimised inside said incubator to allow the growth of the microorganisms sought. Characteristics, such as the temperature, may be regulated so as to be optimal to promote the growth of the target microorganisms. When the assembly formed by the device 1 and the container 40, positioned in the site 30, is introduced into the incubator, the functioning of the arms 11 and 12 may be activated.

Alternatively, and as indicated supra, the device 1 comprises advantageously at least one heating means (3 of FIG. 2), for example at least one contact heating means.

The arms 11 and 12 may be displaced from their first position 22 to their second position 21 (and vice versa). This movement makes it possible to exert a force onto the outer surface of the flexible wall of the container 40 and thus to impose on said container 40 a deformation of this flexible wall. This deformation serves to homogenise, inside the container 40, its contents comprising the sample 51 and the culture medium 52. This homogenisation has the objective of guaranteeing the accessibility of the nutrients in the culture medium to the microorganisms present in the sample, more particularly to the target microorganisms. As indicated previously, the arms 11 and 12 exert a weak-to-moderate force onto the flexible wall of the container in order to enable a homogenisation (also called "soft homogenisation") of the contents and to avoid brutal "kneading", as is the case in the prior art. There results from the weak-to-moderate force exerted onto the flexible wall of the container by the arms 11 and 12 a slight elevation of the level of the contents within the container to a level called the homogenisation level $n_h$ (not depicted in FIG. 1).

The activation of the arms 11 and 12 makes it possible to guarantee a constant movement of said arms 11 and 12 (in a back-and-forth motion), with the aim of continuously homogenising the assembly comprising the sample 51 and the culture medium 52. The arms 11 and 12 may be displaced periodically. The frequency may be chosen and adapted to the sample type and/or to the culture medium type present inside the container 40.

As explained above, the arms 11 and 12 may be displaced in opposite directions and/or in phase opposition (phase alternation) so as to homogenise the assembly consisting of the sample 51 and the culture medium 52. Furthermore, the arms 11 and 12 may also be displaced together (jointly) to modify the level of the fluids present inside the container 40. The functionality of this movement is described with reference to FIG. 5 (cf. infra).

Figure 2:
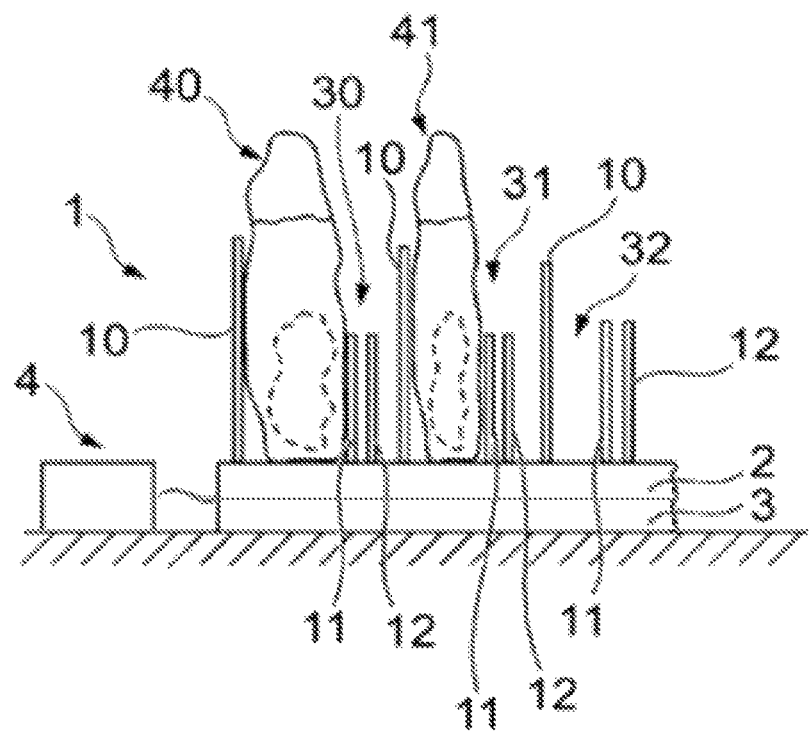
FIG. 2 shows the device from FIG. 1, in lateral view.

FIG. 2 depicts a lateral view of the device 1. The device 1 is depicted with a base 2, a heating element 3, a control element 4, and a first site 30 suitable for receiving a first container 40, a second site 31 suitable for receiving a second container 41 and a third site 32 making it possible to receive a third container (not shown).

The site 30 is delimited by the wall 10 and the set of arms 11 and 12. The site 31 is, in the same way, delimited by a wall 10 and arms 11 and 12. Similarly, the site 32 is delimited by a wall 10 and arms 11 and 12, as is the case for the sites 30 and 31.

The device 1, as depicted in FIG. 2, therefore comprises three sites 30, 31 and 32. One container 40 is received in the site 30, a second container 41 is received in the site 31, the site 32, for its part, being unoccupied.

It should be noted that the device 1 according to the invention comprises at least one site 30 but may advantageously benefit from a large number of sites 30, 31, 32. The device may include 5, 10, 15, 20 or any other quantity of sites 30, 31, 32, depending on the desired use.

Figure 3:
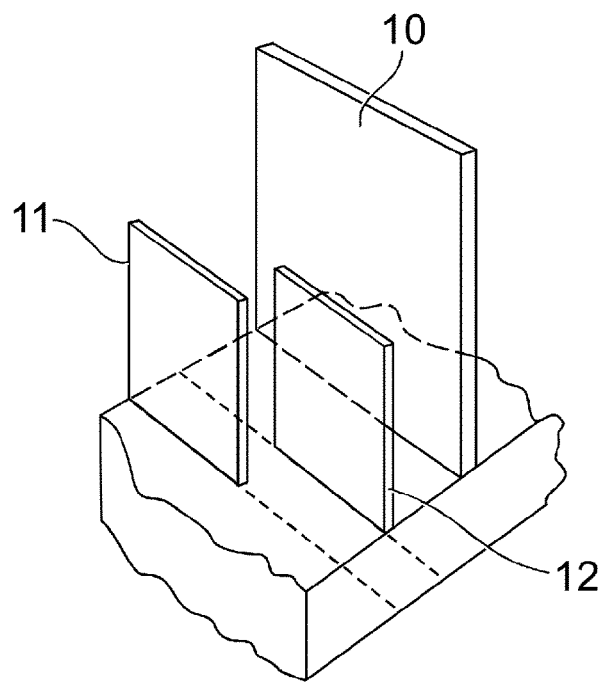
FIGS. 3, 4 and 5 show the functionality of the movable arms (blades) which make it possible to exert a pressure onto a container.
Figure 4:
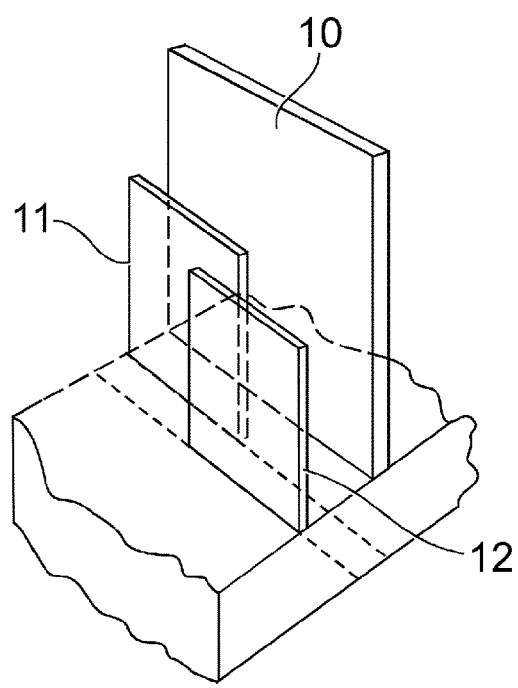
Figure 5:
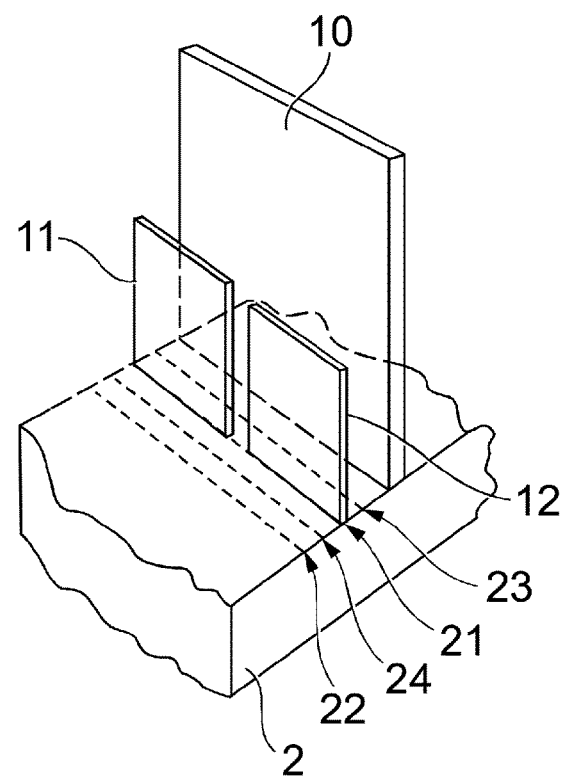

FIGS. 3, 4 and 5 describe more clearly the functioning of the assembly composed of a wall 10 and the arms 11 and 12. For reasons of clarity, no container is depicted on these FIGS. 3, 4 and 5.

FIG. 3 shows the arms 11 and 12, respectively in their first and second positions. The arms 11 and 12 may be displaced from their respective position to the position as depicted in FIG. 4. This means that the arm 11 is displaced from its first position to its second position. Simultaneously, the arm 12 is displaced from its second position to its first position. The arms 11 and 12 are displaced in opposite directions (in phase opposition), which makes it possible for the liquid in a container, which is enclosed between the wall 10 and the arms 11 and 12, to stay substantially at the same level during the movement of said arms 11 and 12. Thus, the level of the liquid varies little during the homogenisation step c) and remains substantially at the height of the homogenisation level $n_h$. However, the movement of the wall 10 of the container imposed by the arms 11 and 12 enables the contents of the container, interposed between the wall 10 and the arms 11 and 12, to be homogenised "softly", and thus enables the violent kneading step, and its disadvantages, to be avoided.

As depicted in FIG. 2, the device 1 makes it possible to homogenise several samples concomitantly, during the first minutes of incubation, preferably between 10 and 60 minutes. Thus, as the homogenisation duration is more significant, the intensity of kneading is considerably reduced. The corresponding advantages are detailed supra.

A better oxygenation of the sample may also be obtained due to this homogenisation, thus allowing an increase in the biomass of the sample.

As depicted in FIG. 5, the arms 11 and 12 may also be displaced together to their second position 21 in order to generate, within the container 40, an elevation of the level of the contents greater than that observed during the homogenisation step c). The technical effect of this embodiment, as well as its advantages, are described with reference to FIGS. 7 to 13.

As mentioned above, the arms 11 and 12 may be displaced to their second position—indicated by reference number 21—but may also be positioned in any other suitable position, indicated by lines 23 and 24. The distance between the wall 10 and the assembly made up of the arms 11 and 12 must be defined with the aim of imposing upon the container 40 a liquid level suitable for the objective sought.

The arms 11 and 12 have been described with reference to FIGS. 1 to 5. It should be noted that the arms 11 and 12 may be replaced by applicators of various forms, provided that they are capable of exerting a certain force on the exterior of a container 40. The arms 11 and 12 may, for example, be replaced by movable walls.

Figure 6:
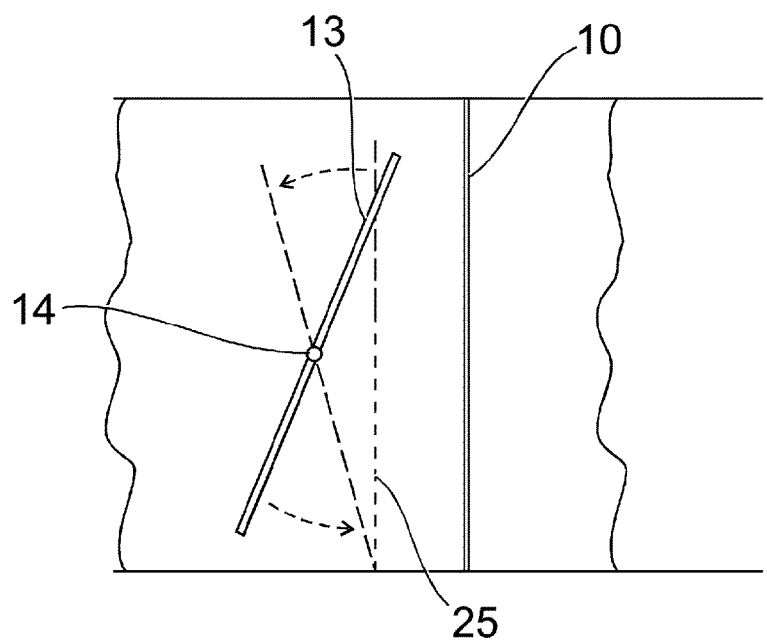
FIG. 6 depicts an alternative embodiment of an applicator which makes it possible to exert a force onto a container.

One alternative embodiment is depicted in FIG. 6, wherein a single applicator 13 may pivot around an axis of rotation 14. By performing a pivot movement, the element 13 may be displaced from the first position as indicated in FIG. 6 to a second position indicated by a dotted line, whilst obtaining the same result as the movement obtained with the arms 11 and 12, and such as explained with reference to FIGS. 3 and 4.

In the position such as shown in FIG. 6, the applicator 13 may be displaced in the direction of the wall 10, for example in the direction of the line 25. Through this movement, the applicator 13 may bring about the modification of the level of the liquid present inside a container 40 situated between the wall 10 and said applicator 13.

Figure 7:
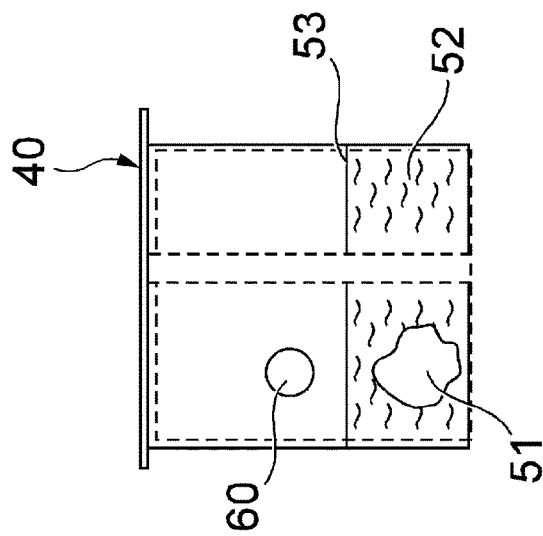
FIG. 7 shows a container containing an assembly consisting of a sample and a culture medium before the recovery of a culture means such as a selective agent (for example an antibiotic)

A container 40 is described in FIG. 7, said container including, inside it, the assembly consisting of a sample 51 and a culture medium 52. Furthermore, the container 40 is equipped with a selective agent (for example an antibiotic) 60 having been positioned inside said container 40, at a level higher than the level 53 of the assembly consisting of the sample 51 and the culture medium 52 (and higher than the homogenisation level $n_h$; not depicted). The container 40 may be placed in the device 1 according to the invention so as to be incubated.

Figure 8:
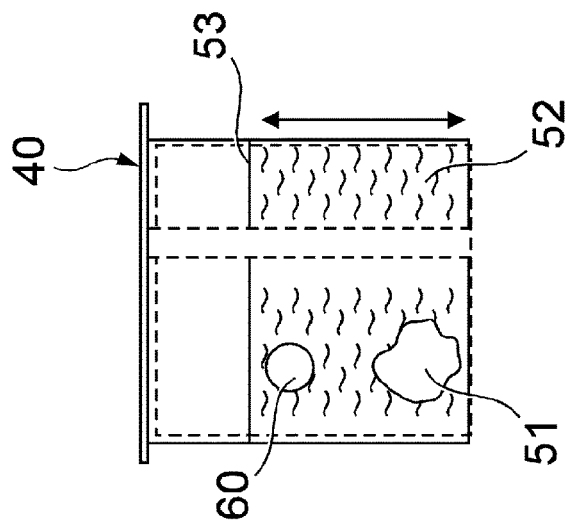
FIG. 8 depicts the container according to FIG. 7 during the recovery of a culture means.

During the period of incubation, the contents of the container 40, that is to say the assembly consisting of the sample 51 and of the culture medium 52, may be, firstly, homogenised with the aid of the arms 11 and 12. In other words, the arms 11 and 12 move between the first and second positions as shown in FIGS. 3 and 4, in phase opposition. After a predefined period of time (depending on the wishes of the user), the arms 11 and 12 may be used so as to exert, together (jointly), a force onto the external wall of the container 40 made of flexible (deformable) material. This force brings about the deformation of the exterior wall of the container 40 and the level 53 of the assembly consisting of the sample 51 and the culture medium 52 increases, from the position such as shown in FIG. 7 to the position such as shown in FIG. 8. In this configuration, the two arms 11 and 12 are both positioned at their second position 21, such as is depicted in FIG. 5. This embodiment is particularly advantageous because it makes it possible to defer the contacting of the contents (comprising a small quantity of target microorganisms, if the latter are present) with the selective agent intended for orienting the growth of the microorganisms toward that of the microorganisms sought. Thus the microorganisms in microbial stress phase are not directly placed in contact with the selective agent, since, at this stage, this risks either slowing their growth and therefore increasing the time necessary for analysis, or totally inhibiting their growth and, thus, impeding their detection/identification.

Indeed, the target microorganisms are referred to as "stressed" when they are present in the sample to be analysed. The microorganisms (including the target microorganisms) need a certain period of time to adapt to the existing conditions inside the container 40. In their so-called "stressed" state, the target microorganisms are particularly sensitive, notably to the presence of selective agents such as antibiotics.

During the incubation phase b), subsequent to the homogenisation step c) and after a predefined period of time sufficient to ensure adequate growth of the microorganisms—and thus to overcome the initial stress phase—an elevation of the level of the contents is generated by the simultaneous displacement of the arms 11 and 12 from their first position 22 to their second position 21 (as depicted in FIG. 5). This level elevation is depicted in FIG. 8. The contents reach a level 53 (n+1), which is higher than the homogenisation level $n_h$. Via this level elevation (from rest level n to level n+1 or from the homogenisation level $n_h$ to this level n+1, depending on the wishes of the user), of the assembly consisting of the sample 51 and of the culture medium 52, the contents of the container 40 may come into contact with the selective agent 60. This means that the selective agent 60 is added to the assembly consisting of the sample 51 and of the culture medium 52, at an opportune moment, i.e. when the microorganisms have been able to overcome the initial stress phase and reproduce by using the nutrients at their disposal in the culture medium.

Concerning the recovery of the element 60, several motions of the liquid to and fro may prove to be advantageous/necessary.

Figure 9:
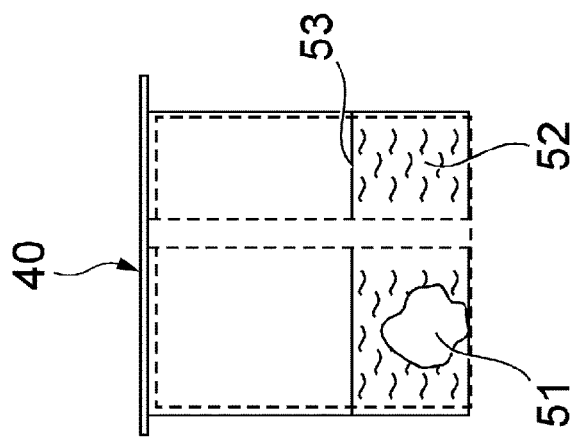
FIG. 9 shows the container according to FIGS. 7 and 8 after the recovery of a culture means.

When the assembly consisting of the sample 51 and of the culture medium 52 has been placed in contact with the selective agent 60, the arms 11 and 12 may be displaced to their first position 22 in order to resume a rest level 53 (level n), such as shown in FIG. 9. Alternatively, a new homogenisation step may be engaged directly after this step, in which case the arms 11 and 12 are displaced in opposite directions and/or in phase opposition (phase alternation) so as to homogenise the assembly consisting of the sample 51, of the culture medium 52 and of the selective agent 60. In this embodiment the level of the contents therefore passes directly from level n+1 to the homogenisation level $n_h$.

Subsequently, and where applicable still during the incubation phase, other steps, for example one or more detection steps may be carried out by elevation of the contents level above level n+1, such that the assembly consisting of the sample 51, of the culture medium 52 and of the selective agent 60 comes into contact with a detection means positioned within the container, above level n+1. This or these detection steps make it possible to reveal the presence or the absence of the target microorganisms.

The device, such as described within FIGS. 1 to 6, is particularly suitable for a microbiological analysis of a food-type sample and, in particular, for a use which makes it possible to detect the presence or the absence of one or more pathogenic microorganisms such as bacteria.

Thus, the functionality which makes it possible to modify the level 53 of the assembly consisting of the sample 51 and the culture medium 52 may also be harnessed to put said assembly into the presence of a sensor-type detection means, such as a biosensor, located inside a container 40. This functionality is described with reference to FIGS. 10 and 11.

Figure 10:
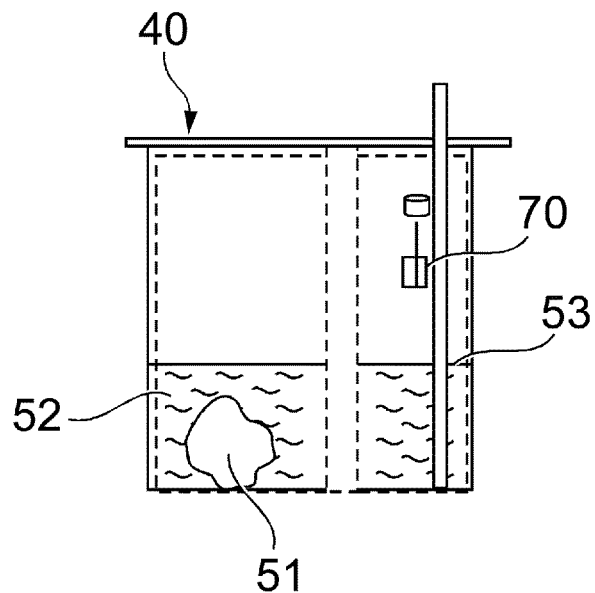
FIG. 10 depicts a container, equipped with a detection means such as a biosensor, before this biosensor is put into the presence of the contents of the container.

FIG. 10 depicts a container 40 comprising, inside it, an assembly consisting of a sample 51 and of a culture medium 52. As shown in this FIG. 10, the detection device (e.g., an optical detection device, a biosensor, etc.) 70 is located at a level situated above the level 53 of the assembly consisting of the sample 51 and of the culture medium 52. More precisely, the biosensor is positioned above the rest level of the contents n and the homogenisation level nh, such that it does not come into contact with the contents during the homogenisation step c). This makes it possible to preserve the integrity of the biosensor and to prevent biological sample residues from interfering unduly with this biosensor. At this stage, the arms 11 and 12 may serve to homogenise the contents of the container 40. At a predetermined moment, the arms 11 and 12 may be used to raise the level 53 to the level as shown in FIG. 11, and thus to place the contents and the biosensor in contact.

Figure 11:
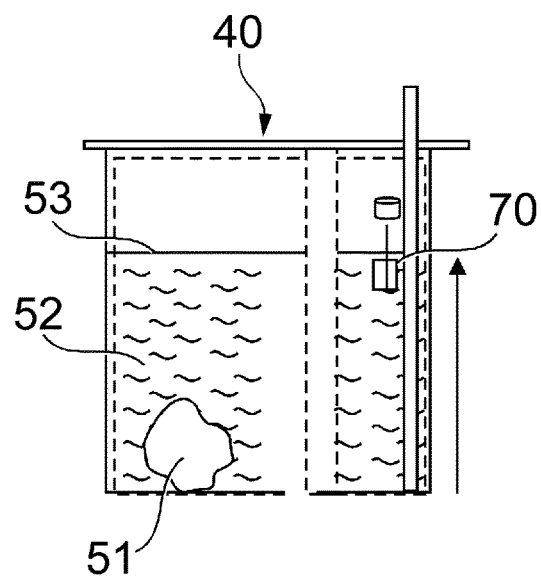
FIG. 11 shows the container according to FIG. 10 wherein, following an elevation of the level of the contents, the latter comes into contact with the biosensor.

As depicted in FIG. 11, the level 53 is sufficient to enable the biosensor 70 to come into contact with the assembly consisting of the sample 51 and of the culture medium 52.

The biosensor is, for example, introduced into the container at the start of the incubation phase. This incubation phase extends, for example, over 24 hours during which the target microorganism concentration will increase progressively. In the first ten hours for example, the target microorganism concentration is too low to interact with the biosensor. Thus, during these first ten hours, and as indicated previously, it is preferable to keep the biosensor apart from the assembly composed of the sample and of the culture medium in order to preserve its integrity and prevent a deterioration of the capacities of said biosensor due to non-specific compounds contained in the sample.

Furthermore, it is possible to place, inside a container 40, a device comprising a culture means such as a selective agent or a reagent, the contents of this device being added to the assembly consisting of the sample 51 and of the culture medium 52, as long as a certain pressure is exerted onto the container 40 containing this selective agent or this reagent. The latter may be, for example, available in a device such as a compartment or a drawer, closed in a first position, which opens under the pressure of one or both arms 11 or 12, in order to allow the mixing of the selective agent or of the reagent, and of the unit consisting of the sample 51 and the culture medium 52.

Figure 12:
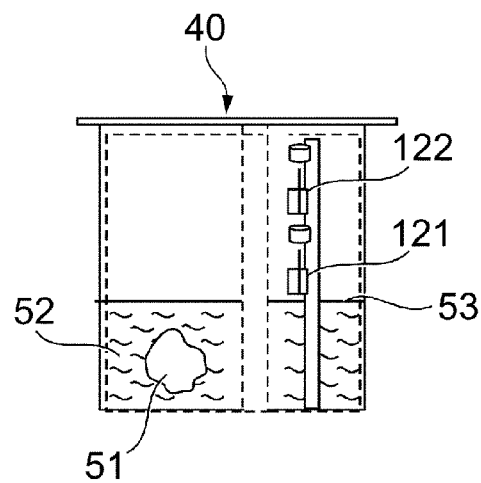
FIG. 12 depicts a container equipped with an assembly consisting of a sample and a culture medium, comprising a first and a second detection means consisting of two biosensors.
Figure 13:
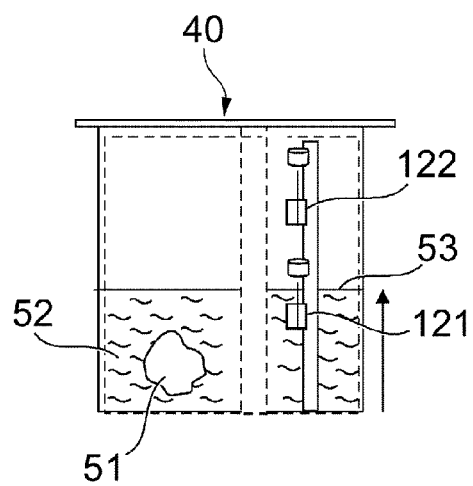
FIG. 13 shows the container according to FIG. 12 after elevation of the level of the contents and placing said contents into contact with the first biosensor, positioned in the chamber of the container, below the second biosensor.
Figure 14:
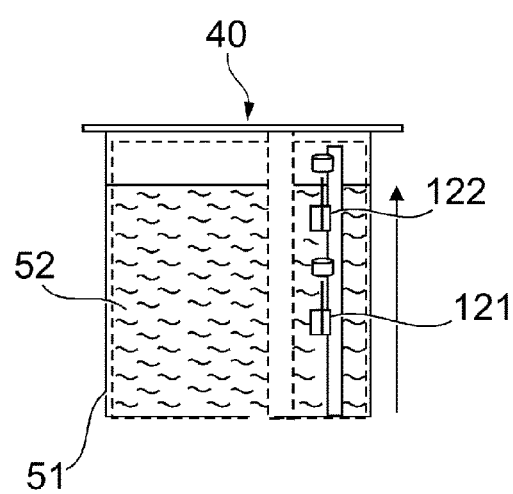
FIG. 14 depicts the container according to FIGS. 12 and 13 after an additional elevation of the level of the contents (of greater magnitude than that depicted in FIG. 13) and placing said contents into contact with the first biosensor, positioned in the chamber of the container, above the first biosensor.

FIGS. 12, 13 and 14 illustrate an alternative use of the method and of the device according to the invention.

FIG. 12 shows a container 40 comprising contents consisting of a biological sample 51 (of food origin, for example) and of a culture medium 52. The contents reach a level 53 inside the container. This level 53 corresponds, in this FIG. 12, to the level of the contents "at rest" n.

The container 40 contains a first biosensor 121 (consisting for example of a solid phase functionalised by an antibody specific to a given bacterial species) and a second biosensor 122 (consisting for example of a solid phase functionalised by a bacteriophage protein specific to said bacterial species or to a different bacterial species), positioned within the container 40, above said first biosensor 121.

Said first and second biosensors are positioned inside the container 40 such that they are out of reach of the contents during the homogenisation step (not depicted), during which the level rises from the rest level n to the homogenisation level $n_h$. When the contents are "at rest" and during the homogenisation step or steps, said first and second biosensors are therefore preserved, namely they are not "polluted"/ "degraded" notably by the matrix debris of the contents.

As depicted in FIG. 13, the level elevation generated by the device according to the invention, from the rest level n to level n+1, situated above levels n and $n_h$ (not depicted), results in the contents being placed in contact with the first biosensor 121, the second biosensor 122 being preserved since it is not immersed. Thus the first biosensor 121 is placed in contact with the microorganisms from the biological sample to be analysed and, if the target bacteria are present amongst said microorganisms, the latter bind to their specific binding partner present on said first biosensor 121, for example to a functionalised antibody. The target bacteria are therefore (immuno) concentrated on the first biosensor 121 and may be identified in situ, for example by immuno-detection techniques well known to the person skilled in the art, implementing revelation systems also well known to him. According to a variant, the identification step is carried out outside the container 40, for example by employing a machine of the VIDAS® type.

In any event, at the end of the identification step, the analysis reveals itself to be either positive (detection and identification of the target bacteria), or negative (absence of detection and identification of said target bacteria).

The level elevation depicted in FIG. 13 may, in practice, consist in a succession of level elevations and falls, from level n or $n_h$ to level n+1 and vice versa. In other words, the contents "lap" the first biosensor 121 in waves, in a pounding and recoiling motion.

Subsequent to the level elevation depicted in FIG. 13, a new level elevation (of greater intensity than that shown in FIG. 13) may be generated by the device according to the invention, from level n, $n_h$, or n+1 to a higher level n+2. This new level elevation step is shown in FIG. 14. During this new level elevation to level n+2, the contents 40 come into contact with the second biosensor 122 (the first biosensor 121 being de facto also immersed). If the target bacteria are present amongst said microorganisms, the latter bind to their specific binding partner present on said second biosensor 122, for example a bacteriophage protein specific to a given bacterial species. The target bacteria are therefore (immuno) concentrated on the second biosensor 122 and may be identified in situ, for example by immuno-detection techniques well known to the person skilled in the art, implementing revelation systems also well known to him. According to a variant, the identification step is performed outside the container 40, for example by employing a machine of the VIDAS® type.

Thus, if a first biosensor 121 comprising a binding partner specific to bacterial species X of a first type, for example an antibody directed against the bacteria X, and a second biosensor 122 comprising a binding partner specific to the bacterial species X of a second type, for example a bacteriophage protein specific to the bacterial species X, are used, the level elevation step depicted in FIG. 13 is carried out in order to attempt to detect and identify the bacteria X after (immuno)concentration on the first biosensor 121. Once a result—positive or negative—has been obtained, the additional level elevation step depicted in FIG. 14 is carried out in order to confirm or to overturn the result obtained after (immuno)concentration on the first biosensor 121. This so-called "confirmation" step is carried out in order to attempt to detect and identify the bacteria X after (immuno) concentration on the second biosensor 122.

It should be noted that a confirmation step of this type may be carried out several hours after the level elevation step depicted in FIG. 13 and proves to be particularly useful when the result obtained after (immuno)concentration on the first biosensor 121 is negative.

Just like the level elevation depicted in FIG. 13, the one depicted in FIG. 14 may, in practice, consist of a succession of level elevations and falls, from level n, $n_h$ or n+1 to the higher level n+2 and vice versa. In other words, the contents "lap" the second biosensor 122 in waves, in a pounding and recoiling motion.

Of course, numerous alternatives can be envisaged, amongst which it is possible to cite (as a non-exhaustive list):

the employment of a first biosensor 121 comprising a binding partner specific to the bacterial species X and a second biosensor 122 comprising a binding partner specific to the bacterial species Y (both binding partners being able to be of the same type or of a different type), the substitution of the first biosensor 121 and/or of the second biosensor 122 with culture means such as an antibody intended for orienting the growth of one or more target microorganism(s).

According to a particular embodiment of the invention, the first biosensor 121 is replaced by at least one antibiotic-type selective agent in the FIGS. 12, 13 and 14 and the reference number 122 still designates a biosensor. According to this particular embodiment, the level elevation step depicted in FIG. 13 makes it possible to place the contents in contact with the selective agent, preferably after a step of homogenising the medium and after incubation (or during incubation) of the contents 40. During this level elevation step, the biosensor 122 is preserved.

Subsequent to this level elevation step (and possibly after a new homogenisation step), the additional level elevation step depicted in FIG. 14 is performed. The contents 40 are therefore in contact with the biosensor 122. As previously, if the target bacteria are present amongst said microorganisms, the latter bind to their specific binding partner present on the second biosensor 122, (for example a bacteriophage protein specific to a given bacterial species). The target bacteria are then (immuno)concentrated on the second biosensor 122 and may be identified in situ, for example by immuno-detection techniques well known to the person skilled in the art, employing revelation systems also well known to him. According to a variant, the identification step is carried out outside the container 40, for example by employing a machine of the VIDAS® type.

Generally, it should be noted that several alternatives are possible for introducing, within the assembly consisting of a biological sample 51 and a culture medium 52, a culture means such as a selective agent.

According to a preferred embodiment, the analysis method according to the invention is a detection method which may be implemented by visually or optically reading a capture support sensitised by a binding partner specific to the microorganism to be detected (for example phage protein, antibody, etc.).

Figure 15:
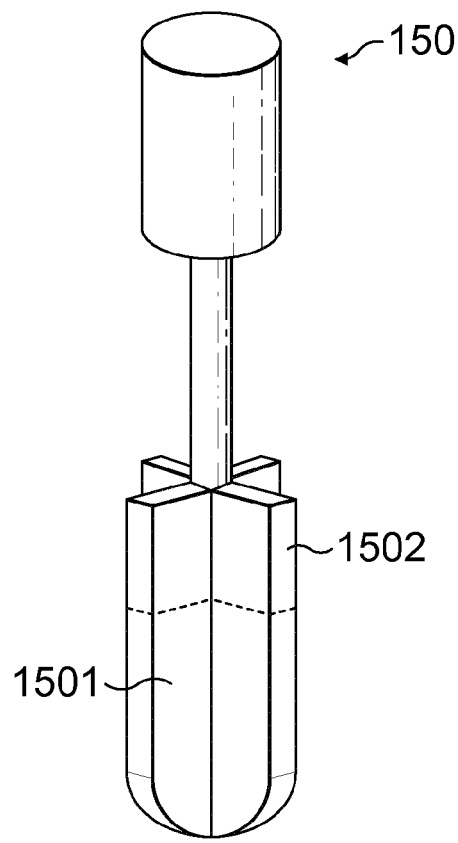
FIG. 15 depicts, schematically, a capture support sensitised (at its capture zone) by a binding partner specific to the target bacteria to be detected (in this case an anti-*Salmonella* recombinant phage protein)
Figure 16:
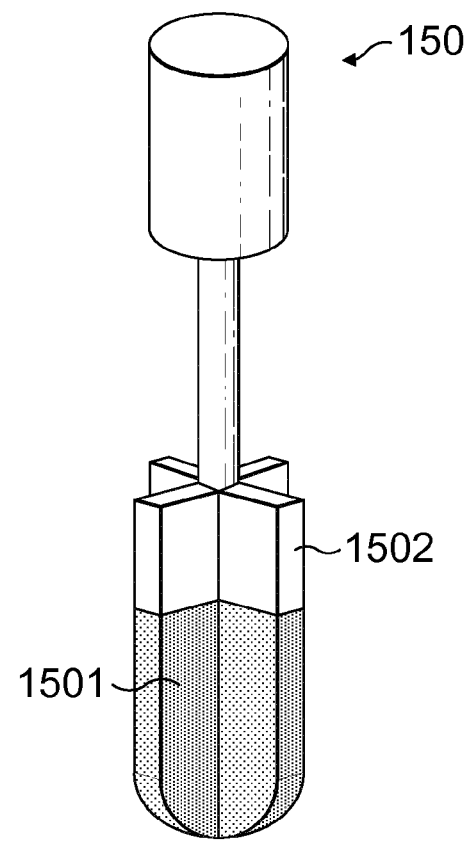
FIG. 16 depicts the sensitised capture support from FIG. 15 after placing in contact with an enrichment medium supplemented with TTC (2,3,5-Triphenyltetrazolium chloride; ref. T8877 SIGMA-ALDRICH), the red coloration at the capture zone revealing the presence of the target bacteria to be detected, FIG. 17 aims to illustrate Example 2 infra and schematically depicts the immersion at $t_0$ of a first capture support of which an example is illustrated in FIG. 15 in two food samples A and B, FIG. 18, also aiming to illustrate Example 2 presented below, depicts, schematically, the placing in contact of a second sensitised capture support with the contents by automatic compression of the bag with the aid of the device according to the invention after 10 h of incubation ($t_0$+10 h).

A preferred example of sensitised capture support is depicted schematically in FIGS. 15 and 16, under the reference 150. The lower part may, advantageously and according to a preferential embodiment, be divided into two zones. The zone labelled 1501 (called the "capture zone") may be sensitised with a solution of binding partners (polyclonal antibodies, monoclonal antibodies, Fab' or Fab'2 fragments, phage proteins, etc.), whereas zone 1502 (called the "control zone") remains free of any binding partner and thus acts as a negative control.

By way of non-limiting example, an appropriate capture support may be made of irradiated polystyrene such as marketed by Nunc/Thermo Scientific (Cat. No. 472230).

The capture support is sensitised (functionalised) by at least one specific binding partner, selected by way of example from antibodies, aptamers, phages, recombinant phage proteins, or any equivalent means which is known to the person skilled in the art and which enables the specific capture of the target bacteria.

Said target bacteria can be coloured simultaneously with their growth due to the revelation system contained in the culture medium. According to a particular example, the revelation system is based on the reduction of TTC (2,3,5-Triphenyltetrazolium chloride; ref. T8877 SIGMA-ALDRICH) by the microorganisms. Simultaneously to the growth, the TTC (colourless in its non-reduced form) is internalised by said microorganisms, then reduced by the latter into triphenyl-formazan (red), thus colouring said microorganisms red and then enabling their revelation on the sensitised capture support, and more precisely in its capture zone referenced 1501 on FIGS. 15 and 16.

The method of detecting microorganisms in a food sample is thus performed by automated or non-automated (preferably automated) visual or optical reading of a sensitised capture support.

Once a certain quantity of coloured target microorganisms has been effectively captured (in case of a positive sample), a change of the optical properties of the support is produced by the appearance of a red coloration thereon (transduction of the biological signal). This coloration of the capture support is therefore detectable to the naked eye and/or via a reading machine such as a camera. When the sensitised capture support 150 (cf. FIGS. 15 and 16) is placed in contact with a medium comprising the target microorganisms, the capture zone 1501 appears coloured (in red) due to the fixation of the target microorganisms onto the specific binding partners. The control zone 1502, which, as its name indicates, acts as a negative control, remains, for its part, the initial colour of the capture support.

In order to facilitate reading, it is preferable that the sensitised capture support is no longer in contact with the contents during the visual or optical reading step. To this end, the device according to the invention is utilised to generate a "fall in level" to the rest level n or homogenisation level nn, such that the capture support emerges during the visual or optical reading step.

According to a preferred embodiment, the device such as described above is suitable for introduction into an incubator, i.e. this may be used in place of the carriers from the prior art with the aim of introducing one or more samples inside this incubator. Compared to these conventional carriers, the device according to the invention—which may be regarded as an "improved carrier" or "intelligent carrier"— makes it possible to carry out a succession of enrichment and/or analysis steps in an automated or semi-automated manner, without superfluous human intervention, all or part of these steps being carried out during the incubation period, hitherto unharnessed.

In a particular embodiment, and as mentioned previously, the device according to the invention comprises means which make it possible to regulate the temperature of the assembly consisting of a sample 51 and a culture medium 52. For example, and with reference to FIG. 2, the device is provided, at its base 2, potentially on the wall 10 and potentially on the blades (arms) 11 and 12, with contact heating means which make it possible to heat said base 2, which in turn heats the container 40 positioned in a site such as the sites 30, 31, 32, etc., thus heating the assembly consisting of a sample 51 and a culture medium 52.

Obviously, a device of this nature equipped with such heating means does not require/no longer requires incubation within an incubator. The device may, for example, be left on a laboratory bench potentially equipped with a cover to prevent heat dispersion. Furthermore, and as explained previously, it will be possible to alter the temperature during incubation and thus benefit from an advantage on the selectivity or on the sensitivity of a test (cf. supra).

The container 40, used in combination with the device 1, may be a container furnished with a transparent outer wall, which facilitates the analysis of the biological processes in progress inside said container. If the container 40 comprises walls made of a transparent material, part of the analysis may be automated with the aid of optical means such as cameras and/or spectrometers.

According to a particular embodiment, after a given incubation period, an aliquot of the contents is transferred into at least one other compartment of the device according to the invention, said at least one other compartment containing one or more selective agents depending on the target microorganism(s).

It should furthermore be noted that it is possible, at the end of incubation, to place the contents in contact with one or more dialysis case(s) comprising at least osmotic compound (for example polyethylene-glycol (PEG)), which will absorb a quantity of water through the dialysis case(s) in order to concentrate the quantity of analytes in solution. According to a particular embodiment, the dialysis case(s) are situated at a higher level than the rest level n and homogenisation level $n_h$, such that the contents are placed in contact with the dialysis case(s) via at least one level elevation step.

The functionality of the invention is illustrated with the (non-limiting) examples presented hereafter.

EXAMPLE 1

Development of a Capture Support Sensitised with at Least One Binding Partner Specific to the Target Microorganism (*S. Napoli*) for the Purposes of Optical Detection An irradiated polystyrene capture support, marketed by Nunc/Thermo Scientific (Cat. No. 472230), is depicted on FIGS. 15 and 16.

The sensitisation of the capture support is carried out in three steps, as follows:
1) the polystyrene support is immersed at 37° C. overnight in a BSA (Bovine Serum Albumin) solution-biotinylated at 5 µg/mL;
2) the support is then immersed at 37° C. for two hours in a streptavidin solution at 10 µg/mL;
3) the support is then immersed for two hours at 37° C. in a solution of specific binding partners (1 µg/mL to 40 µg/mL; the specific binding partner being an anti-*Salmonella* recombinant phage protein).

The sensitised support thus produced may be used for the optical detection of the microorganisms or stored at 2-8° C. with a view to subsequent use.

EXAMPLE 2

Preservation of the Sensitised Capture Support from Example 1 During the First Phase of the Incubation due to Deferred Contacting of Said Capture Support The applicant has discovered, surprisingly, that the deferred placing in contact of the capture support leads to a higher signal being obtained. Indeed the degradation of said capture support (such as the soiling, the loss of bioreceptors, etc.) is manifestly reduced when the latter is immersed for a shorter period of time. When the placing in contact of the sensitised capture support from Example 1 with the cultured biological sample is deferred, this degradation is reduced. Further, the target flora level is particularly high when the capture support is in contact with the sample-culture medium mixture. In consequence, the capture of the target microorganism(s) is then at a maximum.

For the purposes of the present example, the device according to the invention was used. As detailed hereafter, the detection is performed during the incubation period by placing in contact, thanks to the device according to the invention, the lower part of the capture support 150 from Example 1 (sensitised with an anti-*Salmonella* recombinant phage protein) and the contents of a closed container which contains a food sample, diluted to ⅒th in the reaction medium. As mentioned previously, the lower part of the capture support 150 comprises the capture zone 1501 and the control zone 1502.

In order to measure the relative quantity of target bacteria captured in the capture zone 1501, the enrichment medium is supplemented with a cell marker. The marker used is a tetrazolium salt, 2,3,5-Triphenyltetrazolium chloride (TTC; ref. T8877 SIGMA-ALDRICH).

This colourless water-soluble substrate is reduced inside bacteria into an insoluble red compound, formazan. The intensity of the red coloration observed in the capture zone 1501 of the sensitised capture support from Example 1 will therefore be proportional to the number of target bacteria fixed onto said sensitised capture support 150, in the capture zone 1501 (the control zone 1502 remaining, in principle, free from any coloration).

Protocol:
Step 1: Suspension of the Samples in the Reaction Medium
Two samples are prepared as described hereafter.
Samples A. In one container (Stomacher® bag) 25 g of ground beef 15% FM contaminated by 10 colony forming units (CFU) of *S. Napoli* are suspended in 225 ml of BPW ("buffered peptone water", bioMérieux, Cat. No. 42043), supplemented by 0.01 g/l of vancomycin (Sigma, Cat. No. 75423) and 0.4 g/l of TTC (bioMérieux, Cat. No. 04568088).
Samples B. In one container (Stomacher® bag) 25 g of ground beef 15% FM contaminated by 10 colony forming units (CFU) of *S. Napoli* are suspended in 225 ml of BPW (bioMérieux, Cat. No. 42043), supplemented by 0.01 g/l of vancomycin (Sigma, Cat. No. 75423) and 0.4 g/l of TTC (bioMérieux, Cat. No. 04568088).

For each sample, two repetitions have been performed.

Figure 17:
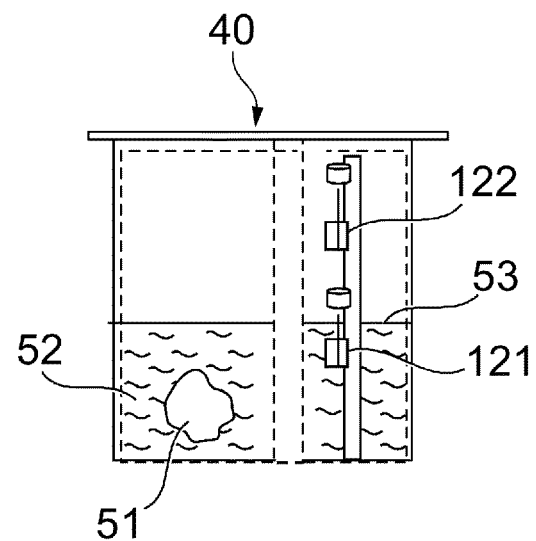
Figure 18:
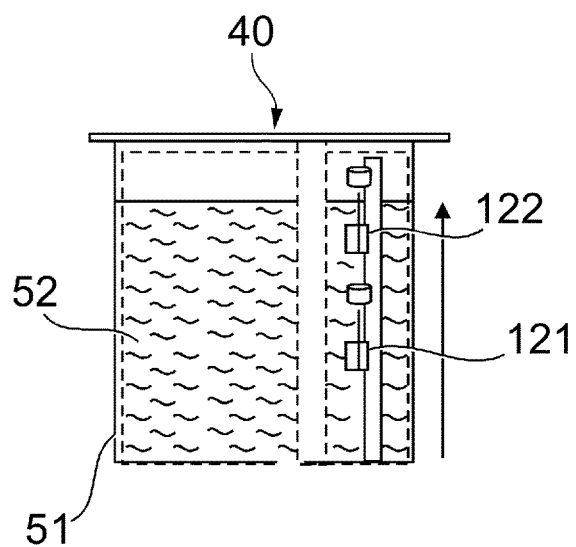

Step 2: Immersion of the Sensitised Capture Supports in the Container before incubation The sensitised capture supports are placed in each Stomacher® bag (samples A and B). The Stomacher® bags are then resealed with the aid of a sealing clip then placed in the device according to the invention and incubated in an oven at 37° C. for 24 h. Thus one of the sensitised capture supports is immersed directly at to in the food sample (as depicted in FIG. 17) and the second is placed in contact with the reaction medium by automatic compression of the bag with the aid of the device according to the invention after 10 h of incubation ($t_0$+10 h), as described below and depicted in FIG. 18.

Step 3: Reading the Capture Supports at the End of the Incubation Period

At the end of the incubation (24 h at 37° C.), and following the non-specific reduction of TTC by all of the bacteria present in the sample (i.e. the additional flora and the target flora), the reaction medium has been coloured red. To be able to observe the sensitised capture supports which reveal the positivity or negativity of the analysed sample, there is a decompression of the device according to the invention (lowering of the level of the fluid inside the container) making it possible to observe the surface of the sensitised capture supports placed in contact with the reaction medium at $t_0$+10 h. For the one immersed at $t_0$, the bag is taken out of the device according to the invention then inclined so as to isolate the support from the reaction medium.

Thus, for the food samples A and B, a low to non-existent red coloration is observed in the capture zone 1501 of the capture supports immersed directly in the food sample at to (contact time 24 h). No red coloration appears in control zone 1502.

On the other hand, the capture supports immersed (placed in contact with the contents) after 10 h ($t_0$+10 h) in each Stomacher® bag (samples A and B) through the device of the invention (cf. FIG. 18) exhibit in their capture zone 1501, a uniform and intense red coloration, thus revealing the presence of salmonellas (*S. Napoli*) in the capture zone 1501 of said sensitised capture supports. No red coloration appears in the control zone 1502.

Thus, the deferred immersion of the sensitised capture support, implemented by the device of the present invention (and depicted in FIG. 18), has made it possible to preserve said capture supports (and in particular their capture zone 1501) against degradation and/or soiling due to prolonged immersion. These capture supports therefore conserved their integrity, thus increasing the quantity of germs captured per surface area unit.

EXAMPLE 3

Example of Use of the Method and of the Device According to the Invention—Immuno-concentration of *Listeria* within the Container (Homogenisation Pouch) then Transfer of the Solid Phase to the VIDAS Machine (Detection of the Presence of *Listeria* in a Food Sample)

3.1 VIDAS *Listeria* LPT Protocol (Prior Art)

The VIDAS *Listeria* LPT protocol is the following: 25 g of food sample are weighed in a plastic pouch, then homogenised with the aid of a Stomacher® for 1 min in 225 ml of enrichment medium (bioMérieux LPT broth ref. 410848). The mixture is then incubated at 30° C. for 26 to 30 hours. At the end of incubation, the sample is manually homogenised and 0.5 ml are sampled and introduced into the VIDAS strip for analysis. As the analysis volume is 0.5 ml, it is necessary to wait for at least 26 hours so that the *Listeria* concentration is sufficient to enable revelation by the VIDAS technique. Furthermore, the sample is mainly composed of non-specific bacteria and matrix debris which interfere with the test sensitivity by generating background noise.

3.2 Protocol According to the Invention 25 g of food sample are weighed in a plastic pouch, then 225 ml of enrichment medium (bioMérieux LPT broth ref. 410848) are added as well as a solid phase functionalised by antibodies and/or recombinant phage proteins directed against *Listeria*. The functionalised solid phase is kept above the level of the liquid. The plastic pouch is directly placed in incubation, at 30° C., in the device according to the present invention which manages the soft homogenisation of the sample during the first hour of incubation. Approximately one hour before the sampling, i.e. after 15 h of incubation, a phase of immuno-concentration of the *Listeria* on the solid phase is triggered by successive "level elevations", namely top-down movements of liquid "lap" the functionalised surface. At the end of 16 hours of incubation, the operator transfers the solid phase directly into the VIDAS machine strip for analysis.

3.3 Comparison of the Two Protocols

The protocol (method) according to the invention has proven to be doubly advantageous. Indeed, it has made it possible:

to considerably reduce the duration of incubation due to the immuno-concentration step from the full volume of the sample (and not from a volume of 500 µL, as is the case in the VIDAS *Listeria* LPT protocol), and to reduce the background noise of the test due to the transfer of a solid phase and no longer of a volume.

The "level elevation(s)" immuno-capture protocol during the incubation may vary depending on the desired duration of contact of the solid phase with the sample.

Furthermore, it may prove advantageous to add to the protocol according to the invention an incubation step subsequent to the "level elevation(s)" immuno-capture protocol in order to enable a colonisation of the solid phase and thus increase the quantity of germs per surface area unit.

Moreover, after immuno-capture, the solid phase can be processed by other methods of detection/analysis such as for example PCR or on an agar medium in a Petri dish.

EXAMPLE 4

Suppression of the Matrix Interference for the Capture and Concentration of Target Microorganisms from a Food Sample It is widely described in the literature that food particles are, amongst others, a limiting factor for the techniques for capturing and concentrating target microorganisms before detection.

The present example aims to establish a comparison between:

i) food samples homogenised with the aid of the device according to the invention (FIG. 1), and ii) the same samples kneaded by implementing a reference method employing a specific instrument, the SMASHER™, marketed by AES (reference AESAP1064), in order to disperse the target bacteria in the culture broth.

After a predefined period of incubation, an immuno-capture step was carried out on a fraction of the culture broth followed by a detection of the pathogen of interest (here *Escherichia coli* O157H7; ref: ATCC 43888) by the PCR (Polymerase Chain Reaction) amplification technique.

Protocol:

Step 1: Suspension of the Samples in the Reaction Medium and Incubation

Eight samples, namely the samples T1 (negative control), A, B, C, T2 (negative control), D, E, F are prepared in the following manner: in a Stomacher® bag-type container, 75 g of ground beef 15% FM (fatty material) are placed in suspension in 225 ml of BPW (bioMérieux, Cat. No. 42043) supplemented by 0.01 g/l of vancomycin (Sigma, Cat. No. 75423).

The four samples (A, B, C, T1) are directly introduced into the device according to the invention (FIG. 1) for "soft" homogenisation for 5 hours at 41° C. The device was programmed with the following parameters:

Speed: 100 m/s
Frequency 1.3 Hz
Amplitude: 10 mm (from 22 mm to 12 mm between the mobile elements (numerical references 11 and 12 in FIG. 1) and the fixed element (numerical reference 10 in FIG. 1))

These parameters ensure displacement of the container's liquid from the rest level n to the homogenisation level $n_h$. The displacement of liquid is thus less than 30%.

The four other samples (D, E, F, T2) are, for their part, kneaded violently for 1 min, by implementing the above-mentioned reference method in force, using the SMASHER™, marketed by AES (reference AESAP1064). Subsequent to this "violent" kneading step, the four samples D, E, F, T2 are introduced into an incubator at 41° C. for 5 hours.

Step 2: Artificial Contamination of Samples A, B, C, D, E and F by *Escherichia coli* O157H7 Ref: ATCC 43888.

The six samples A, B, C, D, E and F are post-contaminated with pathogenic bacteria so as to monitor the concentration before immuno-concentration. The concentration of *Escherichia coli* O157H7 targeted is 10 CFU/ml (the acronym "CFU" signifies "Colony Forming Unit"). Thus, 2250 CFU of *Escherichia coli* O157H7 are introduced into three samples out of four for each of the two experimental conditions, namely in:

samples A, B, C (introduced into the device according to the invention, as depicted in FIG. 1), and
samples D, E, F, (kneaded using the SMASHER™ then incubated at 41° C. for 5 hours).

Of course, the "negative control" samples T1 and T2 were not contaminated with *E. coli* O157H7.

Step 3: Immuno-concentration of *Escherichia coli* O157H7.

Concerning the immuno-capture step, a capture support, namely a 5 cm² non-woven poly(ethylene terephthalate) filter, from a filter bag for a kneader marketed by AES (reference 111 425), was functionalised by a specific binding partner by adapting the three-step protocol described in Example 1.

After incubation, 10 ml of each of the eight samples mentioned above are taken and placed in contact with the capture support for 30 minutes at 41° C. under agitation.

Step 4: Detection of *Escherichia coli* O157H7.

After the capture step, the capture support is rinsed once in EasyMag buffer (bioMérieux ref. 280132) before being heated to 100° C. in order to release the DNA of the lysed cells. The extract is then analysed by PCR by means of the Adiafood *E. coli* O157 kit (ref: DFS6210a).

Step 5: Results.

Table 1 infra, indicating the "cycle threshold" values, namely the number of cycles necessary for the fluorescence value of the probes (CY5 and FAM) to be above the positivity value of the test, is presented hereafter:

TABLE 1

| Homogenisation/kneading mode | Sample | CY5 (Ct) | FAM (Ct) | Interpretation |
|---|---|---|---|---|
| Device according to the invention ("soft" homogenisation) | T1 (negative control) | −1 | −1 | − |
| | A | 34.41432 | 34.96523 | + |
| | B | 34.46399 | 34.75306 | + |
| | C | 34.45198 | 35.29125 | + |
| Smasher ™ ("violent" kneading) | T2 (negative control) | −1 | −1 | − |
| | D | −1 | −1 | − |
| | E | −1 | −1 | − |
| | F | −1 | −1 | − |

In the column headed "Interpretation", the "+" sign denotes a positive result (detection of *Escherichia coli* O157H7), whereas the "−" sign denotes a negative result (absence of detection of *Escherichia coli*; O157H7).

Conclusion

Table 1 supra clearly shows that it was possible to perform the detection of *Escherichia coli* O157H7 at a concentration of 10 UFC/ml only by means of the device according to the invention. Without being bound by the theory, the matrix interference generated by "violent" kneading for 1 minute appears to have impeded the capture—and therefore the detection—of the target pathogen.

The invention claimed is:

1. A device for processing at least one biological sample capable of containing at least one target microorganism within at least one container, said device comprising:
at least one displacement device for generating the displacement of the contents of the at least one container;
at least one site for receiving the at least one container, the at least one container being configured to receive the at least one biological sample within the at least one container wherein the site is delimited by a wall fixed on a base and the at least one displacement device, movable with respect to the base, wherein the at least one container comprises a flexible material to allow the at least one container to be compressed against the wall, wherein the at least one displacement device is movable with respect to the wall to exert a pressure onto the outer surface of the at least one container comprising the flexible material to impose on the at least one container a deformation for generating at least two displacements of the contents of the at least one container at at least two different intensities comprising:
a weakest displacement intensity allowing the homogenization of the at least one biological sample wherein the at least one displacement device is displaced from it/their first position(s) to it/their second position(s), and vice versa, leading the contents of the at least one container to be displaced from a level n, corresponding to a level of the contents at rest, to a homogenization level nh, distinct from the level n, and vice versa and a strongest displacement intensity in a direction of the wall allowing a generation of an increased displacement of the contents to a level n+1, which is different from levels n and nh, such that the contents come into contact with at least one culture, at least one analysis device, or a combination thereof, positioned inside the at least one container, between level n+1 inclusive and level nh exclusive, wherein the at least one displacement device is selected from a movable arm, a movable blade, a movable wall and a moveable applicator.

2. The device according to claim 1, said device comprising an optical detection device configured to detect a presence of said at least one target microorganism.

3. The device according to claim 1, said device comprising a control element configured to alter the at least two different intensities of displacement of the contents.

4. The device according to claim 1, said device comprising at least one heating element configured to incubate the at least one container.

* * * * *